US012521274B2

(12) United States Patent
Tjäder et al.

(10) Patent No.: US 12,521,274 B2
(45) **Date of Patent: *Jan. 13, 2026**

(54) INSERTER FOR AN INTRAUTERINE SYSTEM WITH A LOCKING PART

(71) Applicant: Bayer Oy, Turku (FI)

(72) Inventors: Taina Tjäder, Piispanristi (FI); Mikael Stolt, Vahto (FI); Heikki Salo, Raisio (FI); Mira Piki, Turku (FI); Marina Allen, Turku (FI); Kimmo Laaksonen, Turku (FI); Jari Riski, Parainen (FI); Petri Perälä, Paimio (FI)

(73) Assignee: Bayer Oy, Turku (FI)

( * ) Notice: Subject to any disclaimer, the term of this patent is extended or adjusted under 35 U.S.C. 154(b) by 328 days.

This patent is subject to a terminal disclaimer.

(21) Appl. No.: 17/794,683

(22) PCT Filed: Jan. 20, 2021

(86) PCT No.: PCT/EP2021/051151
§ 371 (c)(1),
(2) Date: Jul. 22, 2022

(87) PCT Pub. No.: WO2021/148443
PCT Pub. Date: Jul. 29, 2021

(65) Prior Publication Data

US 2023/0039977 A1 Feb. 9, 2023

(30) Foreign Application Priority Data

Jan. 24, 2020 (EP) .................................... 20153509

(51) Int. Cl.
*A61F 6/18* (2006.01)
*A61M 31/00* (2006.01)

(52) U.S. Cl.
CPC ............... *A61F 6/18* (2013.01); *A61M 31/00* (2013.01); *A61M 2210/1433* (2013.01)

(58) Field of Classification Search
CPC .... A61F 6/14; A61F 6/18; A61F 6/142; A61F 6/12; A61M 31/00; A61M 2210/1433; A61B 17/42
(Continued)

(56) References Cited

U.S. PATENT DOCUMENTS 3,522,803 A 8/1970 Majzlin
3,842,826 A * 10/1974 Nolan ..................... A61F 6/142 128/840
2023/0042677 A1* 2/2023 Stolt ......................... A61F 6/18

FOREIGN PATENT DOCUMENTS

CA 2816248 A1 * 5/2012 ............. A61B 17/42
CN 1377635 A * 11/2002
(Continued)

OTHER PUBLICATIONS

CN 1377635 A translation (Year: 2002).*
(Continued)

*Primary Examiner* — Caitlin A Carreiro

(57) ABSTRACT

Disclosed is an inserter for an intrauterine system, comprising including a handle body, a measurement tube, a plunger, a flange, a finger holder, and a mechanism for reversibly locking removal thread of the intrauterine system. A proximal end of the measurement tube is movably attached to a distal end of the handle body, and the measurement tube is arranged to remain outside a cervix channel during insertion. The plunger is movably arranged inside the handle body and the measurement tube. The present disclosure also provides a kit comprising the inserter and the intrauterine system.

14 Claims, 24 Drawing Sheets

(58) Field of Classification Search
USPC .......................................... 128/833, 838–840
See application file for complete search history.

(56) References Cited

FOREIGN PATENT DOCUMENTS

| | | | | | |
|---|---|---|---|---|---|
| CN | 204246665 | U | * | 4/2015 | |
| FR | 2806296 | A1 | | 9/2001 | |
| WO | WO-2009122016 | A1 | * | 10/2009 | ............ A61B 34/20 |
| WO | WO-2011154602 | A1 | * | 12/2011 | ........... A61B 5/1076 |

OTHER PUBLICATIONS

CN 204246665 U translation (Year: 2015).*
EPO, Written Opinion for International Patent Application No. PCT/EP2021/051151, May 11, 2021, 5 pages.
EPO, International Search Report for International Patent Application No. PCT/EP2021/051151, May 11, 2021, 3 pages.

* cited by examiner

INSERTER FOR AN INTRAUTERINE SYSTEM WITH A LOCKING PART

CROSS-REFERENCE TO RELATED APPLICATIONS

The present application is the U.S. National Stage filing under 35 U.S.C. § 371 of International Patent Application No. PCT/EP2021/051151, filed on Jan. 20, 2021, which in turn claims priority under 35 U.S.C. § 119 (a) and/or PCT Article 8 to European Patent Application No. 20153509.3, filed on Jan. 24, 2020, which is incorporated herein by references in its entirety.

TECHNICAL FIELD

The present disclosure relates generally to a gynaecological equipment; and more specifically, to an inserter for an intrauterine system. Furthermore, the present disclosure relates to a kit comprising an inserter and an intrauterine system.

BACKGROUND

Intrauterine systems (IUSs) and Intrauterine devices (IUDs) are increasingly gaining popularity as reversible forms of contraception. In the following, the abbreviation IUS is used, and covers both IUS's and IUD's. An inserter is usually used for the positioning of the IUS into the uterus.

Typically, a conventional inserter includes an insertion tube that is usually required to pass through a cervical canal for introducing the IUS into the uterus of a subject. The insertion of the insertion tube in the cervix region is usually a painful experience for the subject due to the anatomical structure of the uterus. For example, the diameter of the insertion tube of a conventional inserter employed to introduce the IUS in the uterus may be incompatible in size with a cervix opening or the overall cervix region (e.g. the tube may have a large cross-sectional area) causing unnecessary pain in the IUS insertion process.

Therefore, in light of the foregoing discussion, there exists a need to overcome the aforementioned drawbacks associated with conventional inserters.

SUMMARY

The present disclosure seeks to provide an inserter for an intrauterine system (IUS). The present disclosure also seeks to provide a kit comprising an inserter and an IUS. The present disclosure seeks to provide a solution to the existing problem of painful insertion of an insertion tube of a conventional inserter in a cervix region of a subject for introducing the IUS into the uterus.

An aim of the present disclosure is to provide a solution that overcomes at least partially the problems encountered in prior art, and provides an improved inserter that is easy-to-use and reduces pain and provides a relatively more comfortable experience during the IUS insertion into the uterus as compared to existing inserters.

In one aspect, an embodiment of the present disclosure provides an inserter for an intrauterine system, comprising

- a handle body having a distal end, a proximal end and a length $L_h$ defined as the distance between the distal end and the proximal end;
- a measurement tube having a distal end and a proximal end, its proximal end being movably attached to the distal end of the handle body, provided the measurement tube is arranged to remain outside a cervix channel during insertion;
- a plunger having a distal end, a proximal end, a length $L_p$ defined as the distance between the distal end and the proximal end, the plunger being movably arranged inside the handle body and the measurement tube, wherein the length $L_p$ is greater than the length $L_h$;
- a flange movably arranged to surround the measurement tube;
- a finger holder movably arranged to surround the handle body; and
- means for reversibly locking a removal thread of an intrauterine system, arranged on the handle body.

In another aspect, an embodiment of the present disclosure provides a kit comprising an inserter as described above and an intrauterine system, wherein the intrauterine system comprises

- a frame having a first end, a second end and a length L defined as a distance from the first end to the second end;
- a removal thread attached to the first end of the frame; and
- at least one pharmaceutically active agent;

wherein the first end of the frame comprises a first locking part and the second end of the frame comprises a second locking part, the first locking part and the second locking part being arranged to form a lock, the removal thread being configured to guide the first locking part to the second locking part.

Embodiments of the present disclosure substantially eliminate or at least partially address the aforementioned problems in the prior art, and enable the disclosed inserter to be conveniently used for positioning of the disclosed IUS into the uterus in painless or less painful manner.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1A:
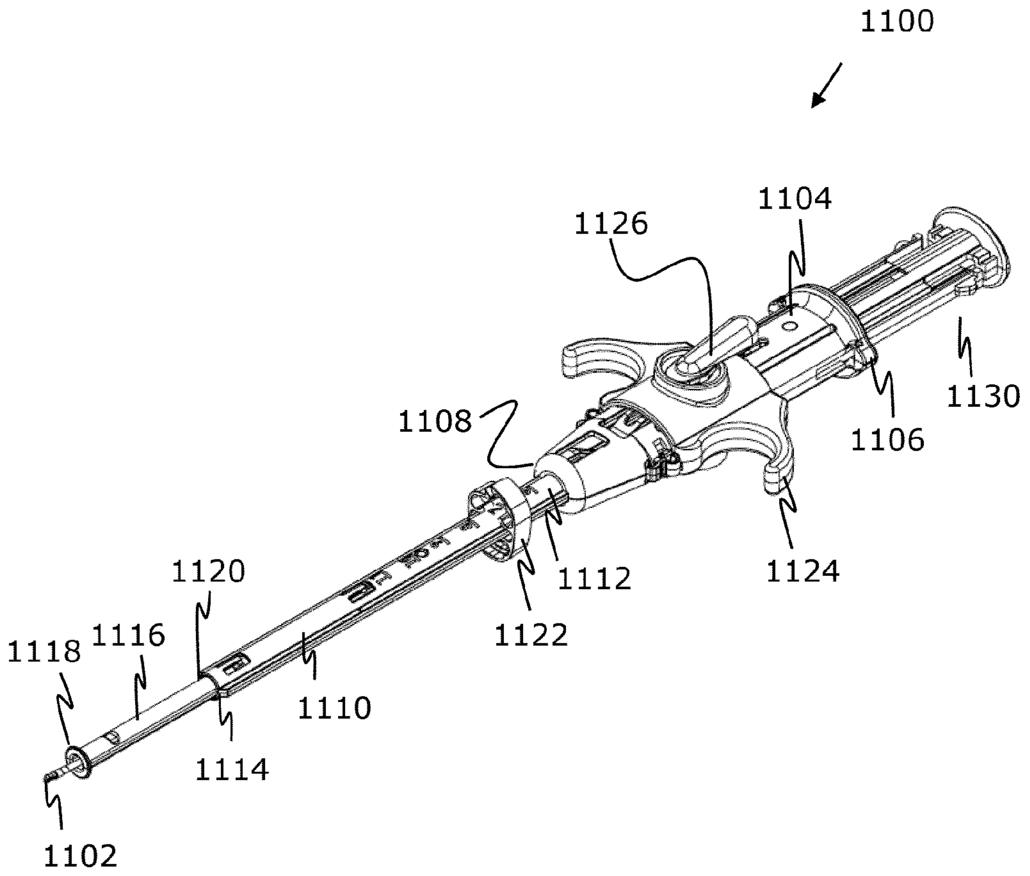
FIGS. 1A-1C are perspective views of an inserter in an assembled and unassembled states, respectively, as well as on an IUS, in accordance with an embodiment of the present disclosure.

In the accompanying drawings, a number relates to an item identified by a line linking the number to the item. When a number is accompanied by an associated arrow, the number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides an inserter for an intrauterine system, comprising

- a handle body having a distal end, a proximal end and a length $L_h$ defined as the distance between the distal end and the proximal end;
- a measurement tube having a distal end and a proximal end, its proximal end being movably attached to the distal end of the handle body, provided the measurement tube is arranged to remain outside a cervix channel during insertion;
- a plunger having a distal end, a proximal end, a length $L_p$ defined as the distance between the distal end and the proximal end, the plunger being movably arranged inside the handle body and the measurement tube, wherein the length $L_p$ is greater than the length $L_h$;
- a flange movably arranged to surround the measurement tube;
- a finger holder movably arranged to surround the handle body; and
- means for reversibly locking a removal thread of an intrauterine system, arranged on the handle body.

In another aspect, an embodiment of the present disclosure provides a kit comprising an inserter as described above and an intrauterine system, wherein the intrauterine system comprises

- a frame having a first end, a second end and a length L defined as a distance from the first end to the second end;
- a removal thread attached to the first end of the frame; and
- at least one pharmaceutically active agent;

wherein the first end of the frame comprises a first locking part and the second end of the frame comprises a second locking part, the first locking part and the second locking part being arranged to form a lock, the removal thread being configured to guide the first locking part to the second locking part.

The present disclosure thus provides the aforementioned inserter and the aforementioned kit for efficiently and conveniently performing the IUS insertion into the uterus. The inserter enables insertion of the IUS in a stable position in the uterus. The inserter is easy-to-use and enables direct entry of the IUS into the cervical canal instead of insertion of any part of the inserter into the cervical canal, to reduce the pain associated with the IUS placement into the uterus. Moreover, a small cross-sectional area of the IUS makes the insertion of the IUS into the uterus almost painless or at least less painful than with conventional IUS's and inserters. Furthermore, the various parts of the inserter are released at a specific time during the IUS insertion process, thereby providing an intuitive and enhanced experience to a healthcare professional while operating the inserter in the IUS insertion process. The use of aforementioned inserter and the kit therefore may enable an increase in an overall rate of successful insertion of the IUS without causing any or only minimal discomfort to the subject.

In the present description, a proximal end is the end that is closest to the user (the medical practitioner) during insertion of the IUS, and a distal end is the opposite end, furthest away from the user.

The inserter comprises a handle body having a distal end, a proximal end and a length $L_h$ defined as the distance between the distal end and the proximal end. The handle body is preferably designed for easy handling of the inserter with a single hand. Moreover, the handle body is preferably designed to be devoid of any handedness preferences. Alternatively stated, the inserter works equally when held using the handle body either with a right hand or a left hand.

According to an embodiment, the handle body is fabricated from a polymeric material (e.g. medical-grade plastics material) and is employable for a single use for hygienic purpose. The handle body may have various shapes and sizes. The handle body is typically a hollow elongated structure, for example, tubular, cylindrical, elliptical, oval, cuboidal, or the like. The handle body acts as a housing and a support structure for various components of the inserter. Moreover, the handle body may be designed to conform to a palm of a medical practitioner. In an example, the handle body has a first cover portion and a second cover portion. Each of the first cover portion and the second cover portion may have a geometrically complementary structure to attach to each other in the assembled state of the inserter. According to an embodiment, the length $L_h$ is 70-110 mm. Optionally, the length $L_h$ of the handle body is around 94 mm. The length $L_h$ is typically from 70, 75, 80, 85, 90, 95 or 100 mm up to 80, 85, 90, 95, 100, 105 or 110 mm.

The inserter further comprises a measurement tube having a distal end and a proximal end. The proximal end of the measurement tube is movably attached to the distal end of the handle body. The measurement tube is a hollow tube-like structure. Optionally, the measurement tube has a circular or oval cross-section.

Optionally, the proximal part of the measurement tube comprises insertion depth indicators, for example on its outer surface. In an example, the insertion depth indicators may refer to calibrated lines with corresponding numerical values marked on the outer surface of a proximal part of the measurement tube. Such insertion depth indicators are used to correctly set the aforementioned flange at a correct position on the measurement tube at the beginning of the IUS insertion process, after the insertion length (i.e. length of the uterus and of the cervical canal) has been measured.

Optionally, the measurement tube is fabricated from a medical grade polymeric material, such as polyethylene, polypropylene, silicone, and the like, or metal. Optionally, the measurement tube may be made of polyether ether ketone, thermoplastic polyurethane, thermoplastic polyurethane elastomer, and the like. It may comprise reinforcing material such as glass fibres.

The inserter further comprises a plunger having a distal end, a proximal end, and a length $L_p$ defined as the distance between the distal end and the proximal end. The plunger is movably arranged inside the handle body and the measurement tube. The length $L_p$ is greater than the length $L_h$. According to an embodiment, the length $L_p$ is 50-90 mm. The length $L_p$ is typically from 50, 55, 60, 65, 70, 75 or 80 mm up to 60, 65, 70, 75, 80, 85 or 90 mm.

According to an embodiment, the plunger is hollow so as to allow the removal thread of the aforementioned intrauterine system to pass through the plunger. The plunger can thus be a thin hollow tube-like structure that allows the removal thread to pass through the plunger. It will be appreciated that the term "removal thread" as used herein refers to one or more threads (namely strings) attached to the IUS at one end and used for removing the IUS at the end of a wearing period (which can be for example 5-7 years). The removal thread is not only used for removal of the IUS, but also to detect whether the IUS is in a correct position within the uterine cavity once the IUS in deployed in the uterus. In an example, the IUS may be preloaded in the inserter in a sales package. In the preloaded state of the IUS, one end of the removal thread remains coupled to the aforementioned first locking part of the IUS, whereas the other end of the removal thread passes through the plunger.

According to an embodiment, the distal end of the plunger is configured to cooperate with the second locking part. Optionally, a portion of the plunger at the distal end may have a form that is geometrically complementary as of the second locking part. Optionally, the plunger is made of a medical grade polymeric material, such as polyethylene, polypropylene, silicone, and the like, or metal.

According to an embodiment, the plunger comprises means for preventing its removal from inside the handle body. The plunger may comprise these means for preventing its removal from inside the handle body at the proximal end of the plunger. In an embodiment, the means has a circumference that is greater than the circumference of the remaining portion of the plunger. Optionally, the means is in the form of a ring or a polygonal shaped part that retains the plunger inside the piston as well as the handle body. The plunger is attached to the distal end inside the piston. Specifically, the plunger is locked between engagement parts of the piston. In an example, the engagement parts of the piston may be small protrusions extending inwards from geometrically opposite directions from the inner surface of the distal part of the piston.

The inserter further comprises a flange movably arranged around the measurement tube. In an embodiment, the insertion depth indicators on the measurement tube allows setting the position of the flange by a user. In the beginning of the IUS insertion procedure, the flange is manually moved to a specified position on the measurement tube with the help of the insertion depth indicators on outer surface of the proximal part of the measurement tube. The specified position refers to the length of the uterine cavity plus the length of the cervical canal measured previously during uterine sounding. Once set on the measurement tube of the inserter, a firm grip of the flange is established with respect to the measurement tube, thereby preventing an unwanted movement of the flange from its initial set position when the inserter is used in the IUS insertion process.

Optionally, the flange comprises a gripping surface on two diametrically opposing sides at an outer portion of the flange. In an example, the gripping surface has a waved structure to enable a firm grip of fingers of a single hand and for pressing an outer part of the flange towards an inner part of the flange for adjusting the flange at a correct position by sliding it over the measuring tube. In such case, the release of the grip then sets the flange in place, and the friction between the flange and the measurement tube allows the flange to remain in its place.

Optionally, the flange has a length Lr. The length Lr is 2-10%, preferably 4-8% of the length L of the measurement tube of the inserter. In an example, Lr may be from 2, 3, 4, 5, 6, 7 or 8 up to 4, 5, 6, 7, 8, 9 or 10% of L. Optionally, the flange is made of a polymeric material, such as low-density polyethylene, high-density polyethylene, polypropylene, thermoplastic polyurethane, thermoplastic polyurethane elastomer, polyether ether ketone and/or a combination thereof. The flange may have various shapes, for example, a rounded rectangular shape, oval, elliptical, round, or the like.

The inserter may further comprise a tip cover having a distal end and a proximal end, and arranged to withdraw inside the distal end of the measurement tube, provided the tip cover is arranged to remain outside the cervix channel during insertion. The distal end of the tip cover has a round bulbous-like structure to prevent the measurement tube from entering into the cervical canal of the subject. The proximal end of the tip cover is movably arranged within an inner surface of the measurement tube at the distal end of the measurement tube. During the insertion of the IUS, when the inserter is pushed towards the subject, the tip cover slides backwards (i.e. towards the handle body), and locks itself on the inner surface of the measurement tube. Optionally, the tip cover is movably attached on the outer surface of the measurement tube and slides over the measurement tube.

The inserter further comprises a finger holder movably arranged to surround the handle body. The finger holder may be used as a support for fingers (e.g. two fingers) to conveniently press the piston towards the distal end of the handle body during the IUS insertion process. According to an embodiment, in the assembled state of the inserter, only the optional tip cover, the flange, and the means (e.g. a thread lock) for reversibly locking the removal thread are movable, and other parts of the inserter are locked. The other parts of the inserter are only released at a specific time during use (i.e. during the IUS insertion process). For example, the finger holder is initially locked in the inserter. Optionally, the finger holder comprises one or more hooks that locks the movement of the finger holder in the inserter. In an embodiment, the finger holder comprises two hooks, such as a first hook and a second hook, which may be locked in corresponding recesses provided in the distal end of the handle body. During the IUS insertion process, once the piston has completely entered the handle body, the finger holder becomes unlocked and moves towards the proximal end of the handle body. Moreover, after the finger holder moves to the proximal end of the handle body, the lock that holds a movement of the measurement tube with respect to the handle body is also released. In an example, one or more clamps may be used to lock the movement of the measurement tube with respect to the handle body. A proximal part of the measurement tube moves inside the handle body until the flange abuts the distal end of the handle body. Thus, the various parts of the inserter are released at a specific time during the IUS insertion process, thereby providing an intuitive and enhanced experience to a healthcare professional as well as a comfortable experience to the subject in the IUS insertion process.

The finger holder may be arranged on the proximal end of the handle body. The finger holder may have one or two ring-shaped or half ring-shaped structure to provide grip for at least two fingers. Alternatively stated, the finger holder may be in the form of circles extending outwards from diametrically opposite sides of the outer surface of the handle body at its proximal end. In such embodiment, the finger holder is movably arranged on the handle body. Optionally, the finger holder is fixedly arranged on the handle body.

The inserter further comprises means for reversibly locking the removal thread of the intrauterine system, arranged on the handle body. According to an embodiment, the means for reversibly locking the removal thread comprises a rotatable knob arranged, in a first position, to lock the removal thread between the handle and the knob and in a second position, to allow the removal thread to be moved with respect to the handle body. Optionally, the knob and the handle body comprise corresponding forms allowing the removal thread to be locked when the knob is in the first position.

In another embodiment, the means for reversibly locking the removal thread may be a roller-like mechanism on which the removal thread is rolled. The rolling of the roller-like mechanism in one direction (e.g. in a forward direction) may lock the removal thread, and the rolling of the roller-like mechanism in another direction (e.g. in a reverse direction) may release the removal thread. In an example, the roller-like mechanism may be a pinion arranged in an opening of the handle body and having a corresponding counterpart.

According to an embodiment, the inserter further comprises a piston attached to the plunger and arranged to move the plunger, the piston being movably arranged inside the handle body. The piston is arranged at the proximal end of the handle body. Moreover, the proximal end of the piston comprises a press member. The press member is provided, for example, for a thumb of the user of the inserter. When the press member of the piston is pushed, the piston enters inside the handle body, and further moves forward towards the distal end of the handle body. In an example, the press member may be integrated to the piston during an injection moulding process. Additionally, the plunger locks between the aforementioned engagement parts of the piston. In the IUS insertion process, the plunger is pushed into the cervical canal and partially into the uterine cavity when the piston is pushed forward towards the distal end of the handle body.

According to an embodiment, the piston is hollow so as to allow the removal thread of the intrauterine system to pass through the piston. The piston is a hollow tube-like structure that allows the removal thread to pass therethrough. In an example, the IUS may be preloaded in the inserter in a sales package. In the preloaded state of the IUS, one end of the removal thread remains coupled to the aforementioned first locking part of the IUS, whereas the other end of the removal thread passes through the plunger and the piston, and emerges from the handle body around the means for reversibly locking the removal thread.

According to an embodiment, the piston comprises means for preventing its removal from inside the handle body. The piston may comprise the means for preventing its removal from inside the handle body at the distal end of the piston. In an example, the means for preventing the removal of the piston from inside the handle body may be at least one protrusion extending from an outer surface of the piston at the distal end of the piston. The at least one protrusion prevents an accidental removal of the piston from the handle body. In another example, two protrusions may be attached to or arranged on the outer surface of the piston. The two protrusions may extend from the outer surface of the piston in two geometrically opposite directions. Optionally, the means for preventing the removal of the piston from inside the handle body may be in the form of a ring that conforms to the inner diameter of the handle body.

According to an embodiment, the IUS insertion process into the uterus (namely, operational stages of the aforementioned inserter when used) is described by taking an example of the IUS having locking parts, and is as follows.

Typically, before insertion, the IUS is at least partly within the inserter (i.e. preloaded in the inserter) and stored in a sales package. The removal thread (which is also the guiding tread) is attached at the first end of the frame of the IUS (i.e. the end that enters the uterus first), and the other end of the removal thread is attached to the handle body. According to an embodiment, the IUS is preloaded on the inserter in such a manner that a small part of the IUS protrudes from the inserter, the rest of the IUS is surrounded and protected by the tip cover. In an example, about 10 mm of the frame is left outside the inserter (i.e. outside the tip cover of the measurement tube) in the preloaded state. The inserter is used in aseptic conditions with a pair of sterile gloves put on by a user (e.g. a health care professional). The insertion process then starts with the adjustment of flange.

A) Flange adjustment: the flange is manually moved at a specified position on the measurement tube with the help of the insertion depth indicators on the outer surface of the measurement tube. The specified position refers to the length of the uterine cavity plus the length of the cervical canal measured previously during uterine sounding. In an example, the gripping surface provided on the two diametrically opposing sides of the flange may be used to press an outer part towards an inner part of the flange.

After the adjustment of flange, the steps slightly vary depending on whether the inserter comprises a tip cover or not. Below, both variants are disclosed (step B for a device without a tip cover, step B" for a device with a tip cover).

B) First IUS insertion stage: the measurement tube is passed through vagina towards the cervix. The inserter is positioned such that the distal end of the measurement tube reaches the cervix opening (i.e. external orifice) and the first end (i.e. the tip) of the IUS is positioned inside the cervix opening. At this stage, the piston is in an extended state and the aforementioned press member of the piston is away from the proximal end of the handle body.

B') First IUS insertion stage: the measurement tube is passed through vagina towards the cervix. The inserter is positioned such that the tip cover reaches the cervix opening (i.e. external orifice) and the first end (i.e. the tip) of the IUS is positioned inside the cervix opening. Thereafter, the whole inserter is gently pushed towards the subject, which makes the tip cover move backwards (i.e. towards the handle body), and a part of the frame (for example about 30 mm) is released from the inserter in the cervical canal. When the tip cover moves backwards, the tip cover locks itself inside the measurement tube. Alternatively stated, the cervix opening prohibits the tip cover from moving forward together with the inserter, and instead forces the tip cover to enter inside the measurement tube, and lock itself in the inner surface of the distal part of the measurement tube. The inserter is gently pushed towards the subject until a resistance from the inserter, typically a physical pressure, is felt by the user. The measurement tube itself is not passed into the cervical canal at any operational stages during the IUS insertion process, thereby decreasing discomfort during the IUS insertion process. At this stage, the piston is in an extended state and the aforementioned press member of the piston is away from the proximal end of the handle body.

C) Second IUS insertion stage: while maintaining a firm contact of the measurement tube (in the case a tip cover is used, a contact of the tip cover, i.e. the tip of inserter) to the portio of the cervix, the piston is pressed from its proximal end towards the distal end of the handle body. The finger holder may be used as a support for fingers (e.g. two fingers) to conveniently press the piston towards the distal end of the handle body. The IUS starts to exit the inserter and to form a loop, under the effect of the removal thread that is held tightly (as it is attached to the handle body). The movement of the piston moves the plunger attached to the piston, which in turn pushes an end (i.e. the aforementioned second locking part) of the frame and thus more frame is released from the inserter into the uterine cavity. Before the piston is entirely inside the handle body, the piston opens a lock of the finger holder, thus allowing its movement. Movement of the finger holder (while the piston and plunger are not moved) makes the IUS to take its final form, but does not move the IUS further inside the uterus. The finger holder also opens a lock of the plunger and piston, where after the action of the user on the piston (pushing it towards the distal end of the handle body) locks the IUS into final shape. The user thus pushes on the piston while maintaining a firm grip on the finger holder, and the locking parts inside the handle ensure the above movements.

Thus, when the finger holder meets the proximal end of the handle body (and also the movement of the piston inside the handle body stops), the IUS is outside the inserter and the locking parts (i.e. the first locking part and the second locking part) of the IUS lock. The piston is locked inside the handle body by finger holder snap hooks, so that a user cannot pull it back. The measurement tube's locking is opened, allowing its movement.

D) Third IUS insertion stage: the whole inserter is pushed towards the patient until the flange meets the handle body. In this stage, a part of the measurement tube moves inside the handle body (i.e. towards the health care professional). This pushes the IUS into correct position in the uterus. In other words, the IUS moves into its fundal position and the whole IUS is accurately positioned within the uterine cavity.

E) Removal thread release and removal of the inserter: the removal thread is released. The removal thread is released by turning the means for reversibly locking the removal thread. In an embodiment, the means for reversibly locking the removal thread comprises a rotatable knob, which is rotated from a first position to the second position, to allow the removal thread to be moved with respect to the handle body, and further allow the release of the removal thread. Optionally, the removal thread is released by pushing a thread cutting button provided on the handle body. When the thread cutting button is pushed, a cutter blade inside the handle body cuts the removal thread. The inserter is positioned such that the removal thread is cut to leave about 2-3 cm visible outside the cervix (i.e. outside the external orifice and about 2-3 cm into vagina to be detectable by touch). The inserter is then pulled out from the subject denoting the completion of the IUS insertion process by the inserter.

It is to be understood that instead of the piston, a different means for moving the plunger may be used in the IUS insertion process, as described above, although the use of the piston makes the operation of the inserter much more convenient. For example, a slider arranged on the handle body may be used to move the plunger. Moreover, in another embodiment, instead of the tip cover moving inside the measurement tube (e.g. in the first IUS insertion stage as described above), the tip cover slides over the distal end of the measurement tube, and locks itself on the outer surface of the measurement tube. In such a case, the tip cover may be required to be made from two parts instead of one part (i.e. in a case where the tip cover withdraws inside the measurement tube, the tip cover is made in one part). Moreover, an additional welding may be required to assemble the two parts of the tip cover on the measurement tube. The present inserter is also suitable for other types of IUS's than what are described here.

The present disclosure also provides a kit comprising an inserter and an intrauterine system (IUS). The inserter for the kit is as described above. The various embodiments and variants described above apply mutatis mutandis to the kit.

The present disclosure thus provides the kit comprising the IUS and the inserter, which enables efficient and convenient insertion of the IUS into the uterus. The IUS is straightened when loaded in the inserter (by the manufacturer) and regains its desired shape upon insertion into the uterine cavity (i.e. when in a deployed state), with the help of the locking parts. Moreover, the disclosed IUS attains a smooth shape, such as a triangular-shape, an annular-shape or a rounded-shape in the deployed state. Such smooth shape of the IUS not only ensures a proper fit of the IUS within the uterus but also reduces the risk of potential perforation of the uterus lining. Moreover, the frame segments, the bending segments, and the locking parts of the IUS enable the IUS to attain a desired continuous smooth shape in its deployed state. Beneficially, the aforementioned IUS provides an intuitive insertion experience for a health care professional. Additionally, the aforementioned inserter of the kit enables an increase in an overall rate of successful insertion of the IUS without causing any or only minimal discomfort to the subject. Furthermore, the risk of uterus penetration during insertion is minimized as the inserter does not include an insertion tube that enters the uterine cavity.

The IUS comprises a frame. The frame has a flexible tubular structure designed to adapt to the anatomical structure of the cervix region as well as the uterine cavity. The flexible structure enables the frame to bend easily into a shape and to withstand strain and stress associated with that shape. For example, the frame may be stretched to almost a straight-line (i.e. a straightened configuration) during insertion of the IUS using the aforementioned inserter (or another suitable inserter), and attains a prespecified shape when placed within the uterine cavity, with the help of the locking parts. Optionally, the frame may have a triangular-shape, an annular-shape, an oval-shape, a circular-shape, a polygonal-shape or an almond-shape in the deployed state.

Optionally, the frame mainly has an essentially round cross-section and the width W is the diameter of the frame. The frame preferably has a smooth cross-section. More optionally, the frame may have oval, or elliptical cross-section to prevent any injuries in the uterine cavity. The width W of the frame may be in a range of 1.5-3.5 mm. The width W is typically from 1.5, 1.7, 1.9, 2.1, 2.3, 2.5, 2.7, 2.9, 3.1 or 3.3 mm up to 1.7, 1.9, 2.1, 2.3, 2.5, 2.7, 2.9, 3.1, 3.3 or 3.5 mm. Beneficially, a smooth round-like cross-section and a small diameter of the frame facilitate frictionless and nearly painless insertion of the IUS into and out of the cervical canal and uterus, and minimises any risk of perforation of the fundus of the uterus. Moreover, the fabrication material of the frame provides the required resilience to the IUS while in use. The resilience of the frame prevents expulsion of the IUS out of the uterine cavity and displacement inside the uterine cavity due to uterine contractions, as the flexible frame balances out the stress caused by the uterine contractions.

Optionally, the frame is manufactured from a material selected from polyethylene, polypropylene, polyether ether ketone and thermoplastic polyurethane. Typically, the frame is made of an inert biocompatible material of an elastomeric composition.

The bending segments, such as the first bending segment and the second bending segment, allow the frame to bend adequately to attain the desired shape. Moreover, the aforementioned removal thread guides the first locking part and the second locking part to lock with each other, which in turn provides the desired shape. In the present description, by a removal thread it is also meant threads in plural. The removal thread is attached in any suitable manner, such as with a knot or by glue.

Optionally, the frame may comprise at least one diagnostic means for locating the IUS in the uterine cavity without a physical intervention. In an example, the at least one diagnostic means may be an X-ray opaque agent, such as barium sulphate, for example, up to 20 wt-% (weight percentage) of the polymeric/elastomeric material of the frame. In another example, the at least one diagnostic means may be a ferromagnetic agent or an agent detectable by ultrasound or fluoroscopic imaging of the IUS in the deployed state. Optionally, the at least one diagnostic means is provided as an inert metal, either coated on at least a part of the frame of the IUS, or provided as a partial metal ring, e.g. made from silver embedded in the IUS.

The frame has a first end, a second end and a length L defined as a distance from the first end to the second end. Typically, the term "first end" refers to the end that is closer to the uterus of a subject during the insertion of the IUS (also called distal end), and the term "second end" refers to the end opposite to the first end, i.e. the end that is closer to the user, such as a health care professional, during the insertion of the IUS by use of an inserter (also called proximal end). Optionally, the length L of the frame ranges from 50-110 millimetre (mm) in a straightened configuration (i.e. when loaded in an inserter). The length L may be typically from 50, 60, 70, 80, 90 or 100 mm up to 60, 70, 80, 90, 100 or 110 mm. The frame of the IUS once deployed in a desired position in the uterine cavity may attain a prespecified configuration (length×width) in a range of 25×23 mm to 31×28 mm, preferably 26×25 mm. In the deployed state, the length is typically from 25, 27 or 29 mm up to 27, 29 or 31 mm. Similarly, in the deployed state, the breadth is typically from 23, 25 or 27 up to 24, 26 or 28 mm. In an example, the configuration of a frame of a triangular-shaped IUS in the deployed state may be 26.6×24.5 mm (length×width). In another example, the configuration of a frame of a triangular-shaped IUS in the deployed state may be 26.2×24.3 mm (length×width).

Furthermore, the first end of the frame comprises a first locking part and the second end of the frame comprises a second locking part, the first locking part and the second locking part being arranged to form a lock. The first locking part and the second locking part extend as overhangs from the first end and the second end of the frame respectively.

Optionally, the first locking part and the second locking part are geometrically complementary structures, such as for example, a hook and a loop, a pin and a loop (or slot), or a clamp and a column. It will be appreciated that the first locking part and the second locking part having the geometrically complementing structures comes in contact with each other in the deployed state in the uterus to engage with each other. The first locking part mechanically interacts with the second locking part for locking of the frame for suitable placement of the IUS into the uterus. While locking, the first locking part is directly held in a non-displaceable manner with the second locking part, consequently locking the frame in a desired shape. While unlocked, the first locking part and the second locking part exist in a disengaged state, for example in a straightened configuration at least partly inside the inserter or in a configuration when the IUS is not yet completely inserted (or released) into the uterine cavity. It will be appreciated that external influences, such as uterine contractions, do not affects the locking of the frame when the first locking part is locked to the second locking part. In an embodiment, the width of the first locking part and the second locking part may be more than the width W of the frame. The width of the first locking part and the second locking part may be in a range of 1.5-4 mm. The width of each of the first locking part and the second locking part is typically from 1.5, 2, 2.5, 3 or 3.5 mm up to 2, 2.5, 3, 3.5 or 4 mm. Notably, the fabrication material of the first locking part and the second locking part makes the IUS including the first locking part, the second locking part highly malleable, and thus the effective width and the largest outer diameter of the IUS is less than 3.7 mm, preferably 2.9 mm.

Optionally, the first locking part is a pin and the second locking part is a loop, wherein the pin is arranged to be irremovably inserted into the loop. The pin and loop engagement ensure a substantial portion of the pin to be engaged in the loop. Preferably, the pin has a knob-like structure and the loop has a complementary recess or opening-like structure for more efficient pin-loop engagement. The pin and loop engagement provide a desired shape to the frame in the deployed state inside the uterus.

Optionally, the first locking part is a hook and the second locking part is a loop, wherein the hook is arranged to be irremovably inserted into the loop. The hook engages with the loop to lock the frame in the desired shape in the deployed state of the IUS inside the uterus. Optionally, the first locking part and the second locking part are made from the same material that is used to make the frame. Optionally, the first locking part is a clamp and the second locking part is a column. The geometrically complimentary structures of the clamp and the column lock with each other in the deployed state inside the uterus.

According to an embodiment, the second locking part is designed to completely contain the first locking part, when the locking parts are locked together. Such an embodiment, when combined with the below discussed inserter, would ensure that the first locking part is not in contact with a plunger of the inserter.

Optionally, the frame comprises a first, a second and a third frame segment having a width W defined as a dimension perpendicular to the length, the first and the second frame segment being connected via a first bending segment and the second and third frame segments being connected via a second bending segment. The width W of the first, the second and the third frame segment is essentially same as the width of the frame. The width W of the first, the second and the third frame segment may be in a range of 1.5-3.5 mm. The width W is typically from 1.5, 1.7, 1.9, 2.1, 2.3, 2.5, 2.7, 2.9, 3.1 or 3.3 mm up to 1.7, 1.9, 2.1, 2.3, 2.5, 2.7, 2.9, 3.1, 3.3 or 3.5 mm. The first bending segment and the second bending segment enable the frame to bend at predefined distances to enable the frame to attain the desired triangular-shape in a deployed state in the uterus. Typically, the bending segments are thinner in at least one dimension than the frame segments, in order to allow them to efficiently bend during insertion, so that the IUS obtains its correct shape. The bending segments (as the whole IUS) however needs to stand forces when the IUS is pulled out, and typically this force is defined as 12 N. Thus, it may be beneficial to make the bending segments wider than the frame segments, in a direction that is perpendicular to the direction when the bending segments are thinner than the frame segments.

According to an embodiment, the first and third frame segments are slightly curved, i.e. they are not completely straight. The radius can be for example 120-155% of the largest dimension of the IUS when it is locked into shape. The radius can thus be for example from 120, 125, 130, 135 or 140% up to 130, 135, 140, 145, 150 or 155% of the largest dimension, such as about 45 mm. This helps the IUS to correctly turn during the insertion, thus minimising discomfort to the patient and uterine wall penetration.

Optionally, the first bending segment is arranged at a first distance D1 from the first end, and the second bending segment is arranged at a second distance D2 from the first end, wherein the first distance D1 is 25-40% of the length L and the second distance D2 is 55-80% of the length L. The first distance D1 is typically from 25, 30 or 35% up to 30, 35 or 40% of the length L. The first distance D1 may be typically from 12.5 to 44 mm, preferably 17.5 to 28 mm. In an example, the first distance D1 is 32-34% of the length L of the frame, i.e. 16 to 37.4 mm. Similarly, the second distance D2 is typically from 55, 60, 65, 70 or 75% up to 60, 65, 70, 75 or 80% of the length L. In an example, the first distance D2 may be from 27.5 to 88 mm, and preferably 38.5 to 56 mm. In an example, the second distance D2 is 65-67% of the length L of the frame, i.e. 32.5 to 73.7 mm.

The first bending segment has a first width W1 and the second bending segment has a second width W2, and the first width W1 may be 5-50 of the width W and the second width W2 may be 5-50% of the width W.

More optionally, the first width W1 is 20-30% of the width W and the second width W2 is 20-30% of the width W. The width W1 is typically from 5, 10, 15, 20, 25, 30, 35, 40 or 45% up to 10, 15, 20, 25, 30, 35, 40, 45 or 50% of the width W. In an example, the width W1 may be from 0.1 to 2 mm, and preferably 0.4 to 1.2 mm. Similarly, the width W2 is typically from 5, 10, 15, 20, 25, 30, 35, 40 or 45% up to 10, 15, 20, 25, 30, 35, 40, 45 or 50% of the width W. For example, the width W2 may be from 0.1 to 2 mm, and preferably 0.4 to 1.2 mm. Thus, the first width W1 and the second width W2 may be substantially identical.

In another embodiment, the first width W1 of the first bending segment and the second width W2 of the second bending segment are larger that the width W of the frame segment. For example, W1 can be 100-150% of W and W2 can independently be 100-150% of W. Indeed, W1 and W2 can be independently selected to be from 100, 105, 110, 115, 120, 125, 130, 135 or 140% up to 105, 110, 115, 120, 125, 130, 135, 140, 154 or 150% W.

Optionally, the cross-section of the frame at the first bending segment and at the second bending segment has an essentially concave shape wherein the first width W1 and the second width W2 is the smallest dimension of the cross-section. The concave shape of the cross-section of the frame at the first bending segment and at the second bending segment allows bending of the IUS. In an embodiment, the cross-section of the frame at the first bending segment and at the second bending segment may have a different shape as long as it allows the frame to bend into the desired shape. For example, a notch may be present on at least one side of each of the first, the second, or the third bending segments and the second bending segment, to allow bending of the frame into the desired shape.

Optionally, the frame comprises a bending point allowing the IUS to be removed. The bending point is a weaker part as compared to the other parts of the frame. In one embodiment, the bending point is provided in a middle section of the frame that does not have locking parts at its end, such as in the middle portion of the second frame segment. Alternatively, the bending point may be provided in any other part of the frame, as long as it facilitates bending or breaking of the frame of the IUS. In an embodiment, during the removal of the IUS from the IUS, when the removal thread is pulled, the IUS is thus bent at the bending point and the circular or triangular shape of the frame thus collapses which allows the removal of the “folded” frame through the cervix channel. The bending point should be designed such that the IUS does not bend in a wrong direction during insertion. In another embodiment, the IUS breaks at the bending point when the removal thread is pulled.

The IUS comprises a removal thread attached to the first end of the frame. The term “removal thread” as used herein refers to a thread (namely a string) attached to the IUS at one end and used for removing the IUS at the end of the wearing period (which is about 3-10 years, preferably 5-7 years). The removal thread is not only used for removal and/or replacement of the IUS at a later time during the wearing period, but also to detect (e.g. as an indication) whether the IUS is in a correct position within the uterine cavity once the IUS in deployed in the uterus. Still further, the removal thread is typically used to hold the IUS in place with respect to the inserter, when in a sales package.

The removal thread is furthermore configured to guide the first locking part to the second locking part. The removal thread guides the first locking part to come in contact to the second locking part and further to engage the first locking part with the second locking part to provide a desired shape to the IUS inside the uterine cavity. Alternatively stated, the removal thread guides the first locking part to the second locking part to engage and lock together when the removal thread is pulled. The strain while pulling the removal thread results in the first locking part to be immovably inserted into the second locking part, consequently locking the frame in the desired shape. Optionally, the first end of the frame has a means for attachment for coupling the removal thread.

Examples of the means for attachment include, but are not limited to an opening, a perforation, a recess, a protrusion, and a notch.

The IUS comprises at least one pharmaceutically active agent. In an example, the pharmaceutically active agent may be a hormone, a drug or drug analogue, an active pharmaceutical ingredient, or a health-promoting substance having contraceptive or other curative properties. Such pharmaceutically active agent functions by either thickening cervical mucus, changing the endometrium making it unsuitable for egg implant, stopping ovulation, or acting as COX1/COX2 inhibitors. In an example, the pharmaceutically active agent may provide and/or enhance protection against various microbial infections, such as a bacterial infection, a fungal infection, and/or a sexually transmitted infection. The IUS may also comprise more than one pharmaceutically active agent.

Optionally, the pharmaceutically active agent is selected from progesterone and its derivatives, oestrogen, progestin, levonorgestrel, cyproterone acetate, desogestrel, etonogestrel, lynestrenol, medroxyprogesterone acetate, norethisterone, norethisterone acetate, norgestimate, drospirenone, gestodene, 19-nor-17-hydroxyprogesterone esters, 17α-ethinyltestosterone and derivatives thereof, 17α-ethinyl-19-nortestosterone and derivatives thereof, ethynodiol diacetate, dydrogesterone, norethynodrel, allylestrenol, medrogestone, norgestrienone, ethisterone and dl-norgestrel; and androgenic steroids, such as danazol and gestrinone; naproxen, ibuprofen, mefenamic acid, flurbiprofen, indomethacin, diclofenac, piroxicam, meloxicam, ketoprofen, gonadotropin-releasing hormone agonists, progesterone receptor antagonists such as mifepristone (11β-4-dimethylaminophenyl-17β-hydroxy-17α-propinyl-4, 9-estradiene-3-one); ulipristale acetate, (11β,17β)-17-Hydroxy-11-[4-(methylsulphonyl)phenyl](pentafluoroethyl)-estra-4,9-dien-3-one, 17α-acetoxy-11β-[4-(N,N-dimethylamino)phenyl]-21-methoxy-19-norpregna-4,9-diene-3,20-dione, 17α-acetoxy-11β-(4-N,N-dimethylaminophenyl)-19-norpregna-4,9-diene-3,20-dione, 11β-(4-acetylphenyl)-17β-hydroxy-17α-(1,1,2,2,2-pentafluoroethyl)-4,9-estradiene-3-one, asoprisnil (benzal dehyde-4-[(11β,17β)-17-methoxy-17-(methoxymethyl)-3-oxoestra-4,9-dien-11-yl)]-1-oxime).

As hormones, for example levonorgestrel can be used, and as COX inhibitor, indomethacin may be used. It will be appreciated that the pharmaceutically active agent is administered at a suitable amount, for example in a maximum feasible amount suitable to a subject. Moreover, the amount (i.e. dosage) of the pharmaceutically active agent varies depending on the particular pharmaceutically active agent, intended use, action time, release rate and therapy period as well as the age and medical condition of the subject. Furthermore, the pharmaceutically active agent typically has a pH level that is suitable for the uterus. Thus, the IUS functions not only as a long-acting reversible contraceptive method but may be used for a variety of other applications, such as treating a medical condition, swelling, pain in the uterus, depending upon the pharmaceutically active agent supplied via the IUS.

Optionally, at the least one pharmaceutically active agent is arranged in the frame. In an example, the at least one pharmaceutically active agent is dispersed or dissolved in the material of the frame before its manufacturing. In an embodiment, the at least one pharmaceutically active agent is provided in one of the three frame segments, i.e. the first, the second, or the third frame segment. In another embodiment, the at least one pharmaceutically active agent is provided in all the three frame segments.

Optionally, the at least one pharmaceutically active agent is arranged in at least one capsule, the capsule being arranged to surround the frame on at most a part of its length L. Specifically, the at least one capsule is a drug container comprising the pharmaceutically active agent. The at least one capsule arranged to surround the frame may also provide a required stiffness to the frame of the IUS at such part of the frame's length. The at least one capsule is arranged to surround at least one of the first, the second, or the third frame segment, leaving the first locking part, the first bending segment, the second bending segment and the second locking part free from the at least one capsule.

Optionally, the at least one capsule is arranged to surround the frame along its whole length with the exception of the first locking part and the second locking part. The at least one capsule is arranged to surround the first, the second, and the third frame segments. In such a case, the at least one capsule is flexible enough to bend at the bending segments.

Optionally, the at least one capsule is manufactured from poly(dimethyl silicone), siloxane based elastomer, a thermoplastic polyurethane, a thermoplastic polyurethane elastomer, ethyl vinyl acetate, a polyolefin-based elastomer, a silicone containing thermoplastic, polyurethane, polylactic acid and polycaprolactone. More optionally, the at least one capsule is manufactured from a biocompatible polymer matrix. Examples of the biocompatible polymer matrix include, but are not limited to copolymers of dimethylsiloxanes and methylvinylsiloxanes, polyethylene, polypropylene, polybutadiene, polyisoprene, acrylic acid polymers, ethylene/propylene copolymers, ethylene/ethyl acrylate copolymers, poly(methacrylate), polymethyl methacrylate, styrene-butadiene-styrene block copolymers, styrene-isobutylene-styrene copolymers, poly(hydroxyethylmethacrylate), polyethers, polyacrylonitriles, polyethylene glycols, polymethylpentene, polyhydroxy alkanoates, polyorthoesters, hydrophilic polymers (such as hydrophilic hydrogels), cross-linked polyvinyl alcohol, polytetrafluoroethylene, polyvinyl chloride, polyvinyl acetate, neoprene rubber, and butyl rubber.

In an embodiment, the at least one capsule is selected from a matrix system and a core-membrane system. In an example, the matrix system may be a polymer matrix, such as a siloxane-based elastomer, with the pharmaceutically active agent dispersed or dissolved therein. In another example, in the core-membrane system, the at least one capsule may comprise a pharmaceutically active agent core, and a membrane encasing the pharmaceutically active agent core. The core may be a hollow tube-like structure assembled on the frame (surrounding the frame on at most a part of its length L) to deliver the pharmaceutically active agent at a controlled rate in the uterus. The membrane may be a permeable layer, made up of an inert material, that prevent direct contact between the pharmaceutically active agent and the biological fluid in the uterus. Furthermore, the membrane layer may adjust the release rate of the pharmaceutically active agent by acting as a diffusion layer surrounding the pharmaceutically active agent core. In an embodiment, the membrane may surround the at least one capsule from all directions, resulting in a closed capsule. In another embodiment, the at least one capsule is not completely surrounded by the membrane. In an embodiment, the membrane is more permeable and allows the pharmaceutically active agent to contact the biological fluids as compared to the pharmaceutically active agent core.

Optionally, a cross-section of the at least one capsule is selected from circular and oval. For example, the capsule may have a round, circular, an oval or an elliptical cross-section as long as the shape is suitable to be inserted into the cervical canal and into the uterus. Optionally, the outer diameter of the capsule is in a range of 2-3.5 mm, and preferably about 2.9 mm. The outer diameter of the capsule is typically from 2, 2.1, 2.3, 2.5, 2.7, 2.9, 3.1, or 3.3 mm up to 2.1, 2.3, 2.5, 2.7, 2.9, 3.1, 3.3 or 3.5 mm.

Optionally, the IUS comprises at least two capsules. In an example, the at least two capsules are placed at a predefined distance from each other on the frame. Preferably, the at least two capsules are not in contact with each other once the IUS is inserted into the uterine cavity. Optionally, the number of capsules may be 3, 4, and so forth, depending on the different types of therapeutic agents to be administered.

Optionally, the IUS comprises a first capsule arranged to surround the first frame segment, a second capsule arranged to surround the second frame segment and a third capsule arranged to surround the third frame segment, wherein the first locking part, the first bending segment, the second bending segment and the second locking part are free from capsules. In this embodiment, the first capsule, the second capsule and the third capsule may impart sufficient stiffness to the frame during the insertion process and further help the IUS to attain a desired continuous smooth shape (i.e. a prespecified configuration) in its deployed state. The first locking part, the first bending segment, the second bending segment and the second locking part are void of capsules in order to cause necessary bends in and/or shaping of the frame of the IUS.

Optionally, the capsules comprise different pharmaceutically active agents. Optionally, the first capsule, the second capsule and the third capsule may be identical or different in structure, and may contain same or different pharmaceutically active agents. In an example, the first capsule may include a first pharmaceutically active agent, such as progestin, the second capsule may include a second pharmaceutically active agent, such as diclofenac, and the third capsule may include a third pharmaceutically active agent, such as levonorgestrel. Furthermore, the release of the pharmaceutically active agents from the at least two capsules may be carried out simultaneously or one after another depending upon a rate of release of the pharmaceutically active agents to be achieved and their respective interactions with the biological fluid in the uterus.

Optionally, a first pharmaceutically active agent is arranged in a capsule, the capsule being arranged to surround the frame on at most a part of its length L, and a second pharmaceutically active agent is arranged in the frame. The capsule affects the rate of release of the pharmaceutically active agent in the uterus. The at least one pharmaceutically active agent dispersed or dissolved in the fabrication material of the frame has a rate of release of the pharmaceutically active agent different from the rate of release of the pharmaceutically active agent arranged in the capsule. It will be appreciated that the rate of release of the pharmaceutically active agent depends upon the permeability of the fabrication material of the frame and/or the capsule.

According to an embodiment, the frame is obtained by an injection moulding process. One capsule is arranged to surround a part of the frame that forms a capsule-frame assembly. However, in cases where there is more than one capsule, the capsules may be arranged anywhere on the frame, leaving at least the first locking part and the second locking part free from the capsule, depending on the desired shape of the IUS to be achieved.

In another exemplary aspect, an embodiment of the present disclosure provides an intrauterine system comprising a frame having a first end, a second end and a length L defined as a distance from the first end to the second end;

a removal thread attached to the first end of the frame; and a copper wire arranged around at least a part of the frame;

wherein the first end of the frame comprises a first locking part and the second end of the frame comprises a second locking part, the first locking part and the second locking part being arranged to form a lock, the removal thread being configured to guide the first locking part to the second locking part.

According to this embodiment, the copper wire arranged around at least a part of the frame functions as a contraceptive by preventing fertilization of an egg by sperm. The copper IUS (i.e. the IUS comprising copper) is hormone free and therefore a good option for women who prefer or are advised a non-hormonal birth control method due to medical reasons.

According to an embodiment, the IUS is pre-installed (or preloaded) in the inserter in a sterile sales package. The sales package protects the contents of the kit from environmental and mechanical factors.

DETAILED DESCRIPTION OF THE DRAWINGS

Referring to FIG. 1A, there is shown a perspective view of an inserter 1100 in an assembled state preloaded with an IUS 1102, in accordance with an embodiment of the present disclosure. The inserter 1100 comprises a handle body 1104 having a proximal end 1106 and a distal end 1108. The inserter 1100 further comprises a measurement tube 1110 having a proximal end 1112 and a distal end 1114. The proximal end 1112 of the measurement tube 1110 is movably attached to the distal end 1108 of the handle body 1104. The inserter 1100 further comprises a tip cover 1116 having a distal end 1118 and a proximal end 1120. The tip cover 1116 is arranged to withdraw inside the distal end 1114 of the measurement tube 1110. The inserter 1100 further comprises a flange 1122 movably arranged around the measurement tube 1110. A finger holder 1124 is movably arranged to surround the handle body 1104. The inserter 1100 further comprises a means 1126 for reversibly locking a removal thread of the IUS 1102. The means 1126 for reversibly locking the removal thread is arranged on the handle body 1104. The inserter 1100 further comprises a piston 1130 that is movably arranged inside the handle body 1104.

Figure 1C:
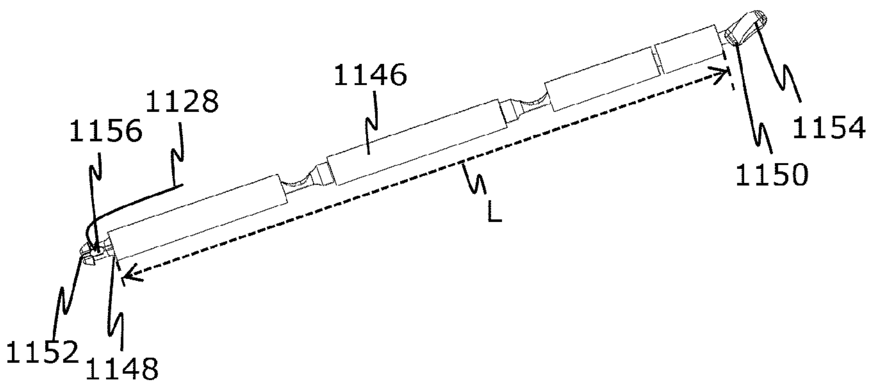
Figure 1B:
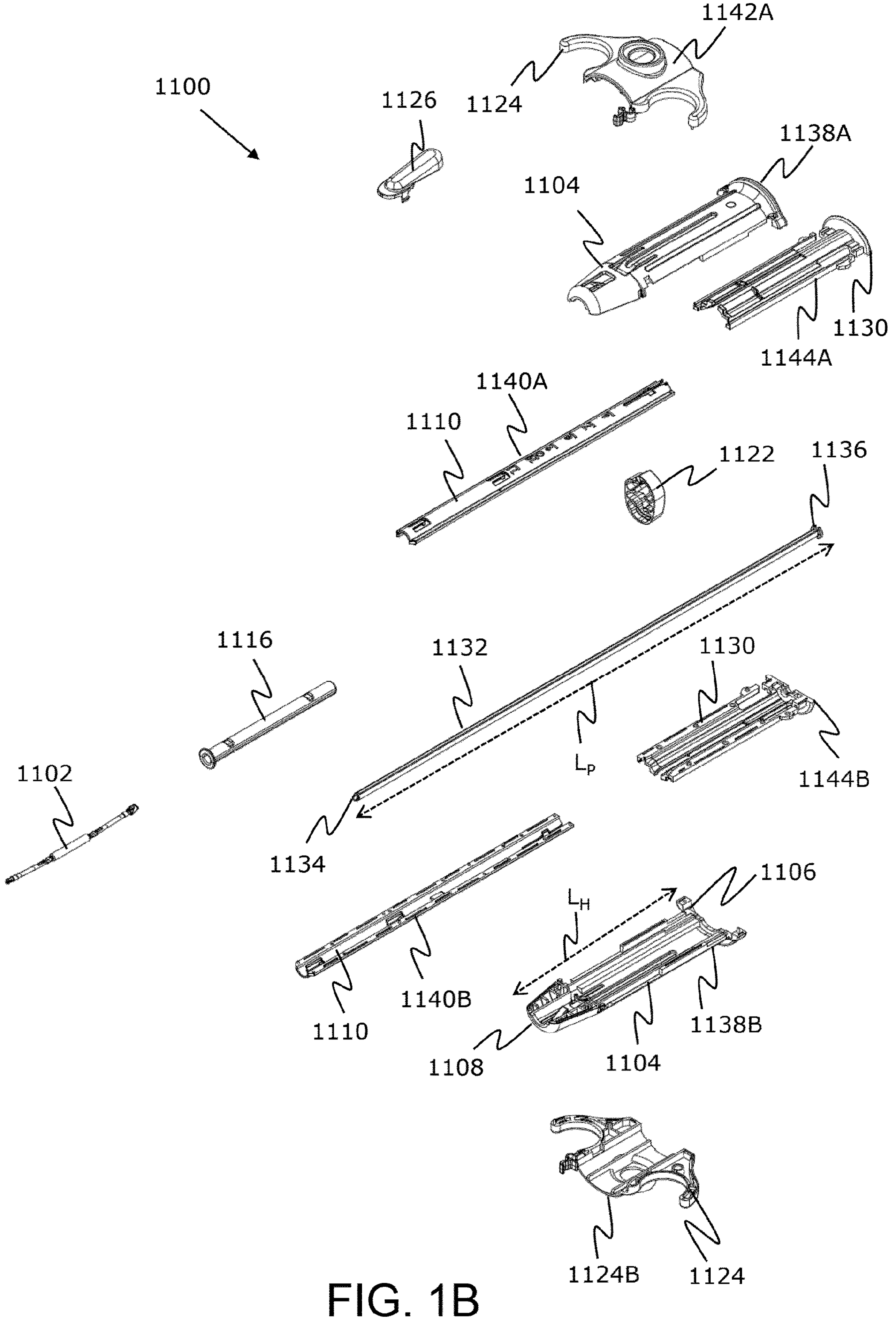

Referring to FIG. 1B, there is shown a perspective view of the inserter 1100 of FIG. 1A in an unassembled state with the IUS 1102, in accordance with an embodiment of the present disclosure. The inserter 1100 further comprises a plunger 1132 having a distal end 1134, a proximal end 1136, and a length $L_p$ defined as the distance between the distal end 1134 and the proximal end 1136. In the assembled state of the inserter 1100, the plunger 1132 is movably arranged inside the handle body 1104 and the measurement tube 1110. Further, shown is a first cover portion 1138A and a second cover portion 11388 of the handle body 1104. The handle body 1104 has a length $L_h$ defined as the distance between the distal end 1108 and the proximal end 1106. Notably, the length $L_p$ is greater than the length $L_h$. Further, shown is a first part 1140A and a second part 114013 of the measurement tube 1110, a first part 1142A and a second part 11428 of the finger holder 1124, and a first part 1144A and a second part 11448 of the piston 1130. Further, shown is the flange tip cover 1116 and the means 1126 for reversibly locking the removal thread of the IUS 1102. In the assembled state of the inserter 1100, the tip cover 1116 accommodates the frame

1146 of the IUS 1102 in the straightened configuration (i.e. in a preloaded state of the IUS 1102 in the inserter 1100 before the insertion of the IUS 1102 into the uterus). Further, shown is the flange 1122, the finger holder 1124, and the means 1126 for reversibly locking a removal thread of the IUS 1102.

Further, FIG. 1C shows an enlarged view of the IUS 1102. The IUS 1102 comprises a frame 1146 having a first end 1148 and a second end 1150, and a length L is defined as a distance from the first end 1148 to the second end 1150. The frame 1146 is straightened and stretched when loaded in the inserter 1100 in the assembled state, before inserting the IUS 1102 into the uterus. The first end 1148 of the frame 1146 comprises a first locking part 1152 and the second end 1150 of the frame 1146 comprises a second locking part 1154. In this embodiment, the first locking part 1152 is a pin and the second locking part 1154 is a loop. The first locking part 1152 and the second locking part 1154 have complementary structures to enable the pin to be irremovably inserted into the loop. The first locking part 1152 at the first end 1148 of the frame 1146 comprises an opening 1156 for receiving the removal thread 1128.

Figure 2A:
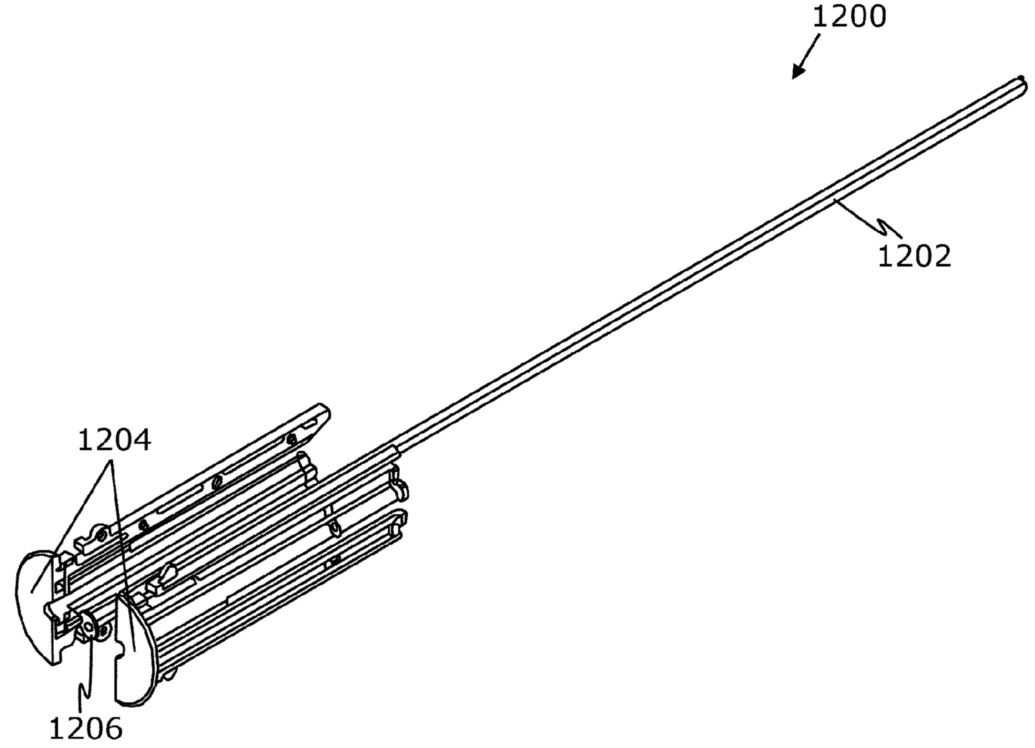
FIG. 2A illustrates a perspective view of a piston and plunger subassembly of an inserter, in accordance with an embodiment of the present disclosure.

Referring to FIG. 2A, there is shown a perspective view of a piston and plunger subassembly 1200 of an inserter, in accordance with an embodiment of the present disclosure. In the piston and plunger subassembly 1200, there is shown an arrangement of a plunger 1202 within a piston 1204. The plunger 1202 comprises a means 1206 for preventing its removal from inside a handle body and the piston 1204 of the inserter.

Figure 2B:
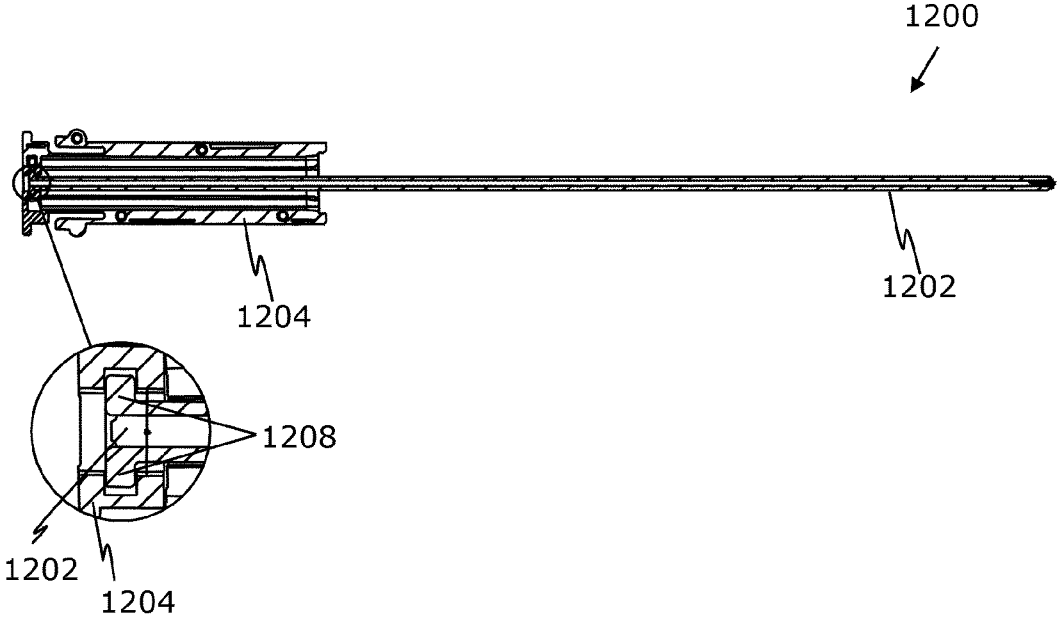
FIG. 2B illustrates a cross-sectional view of a piston and plunger subassembly with engagement parts of a piston of an inserter, in accordance with an embodiment of the present disclosure.

FIG. 2B shows a cross-sectional view of a piston and plunger subassembly 1200 of an inserter, in accordance with an embodiment of the present disclosure. In the piston and plunger subassembly 1200, the plunger 1202 is attached to the piston 1204. Further shown, is an enlarged view of a distal portion of the piston and plunger subassembly 1200 to depict engagement parts 1208 of the piston 1204. The plunger 1202 locks between the engagement parts 1208 of the piston 1204.

Figure 3A:
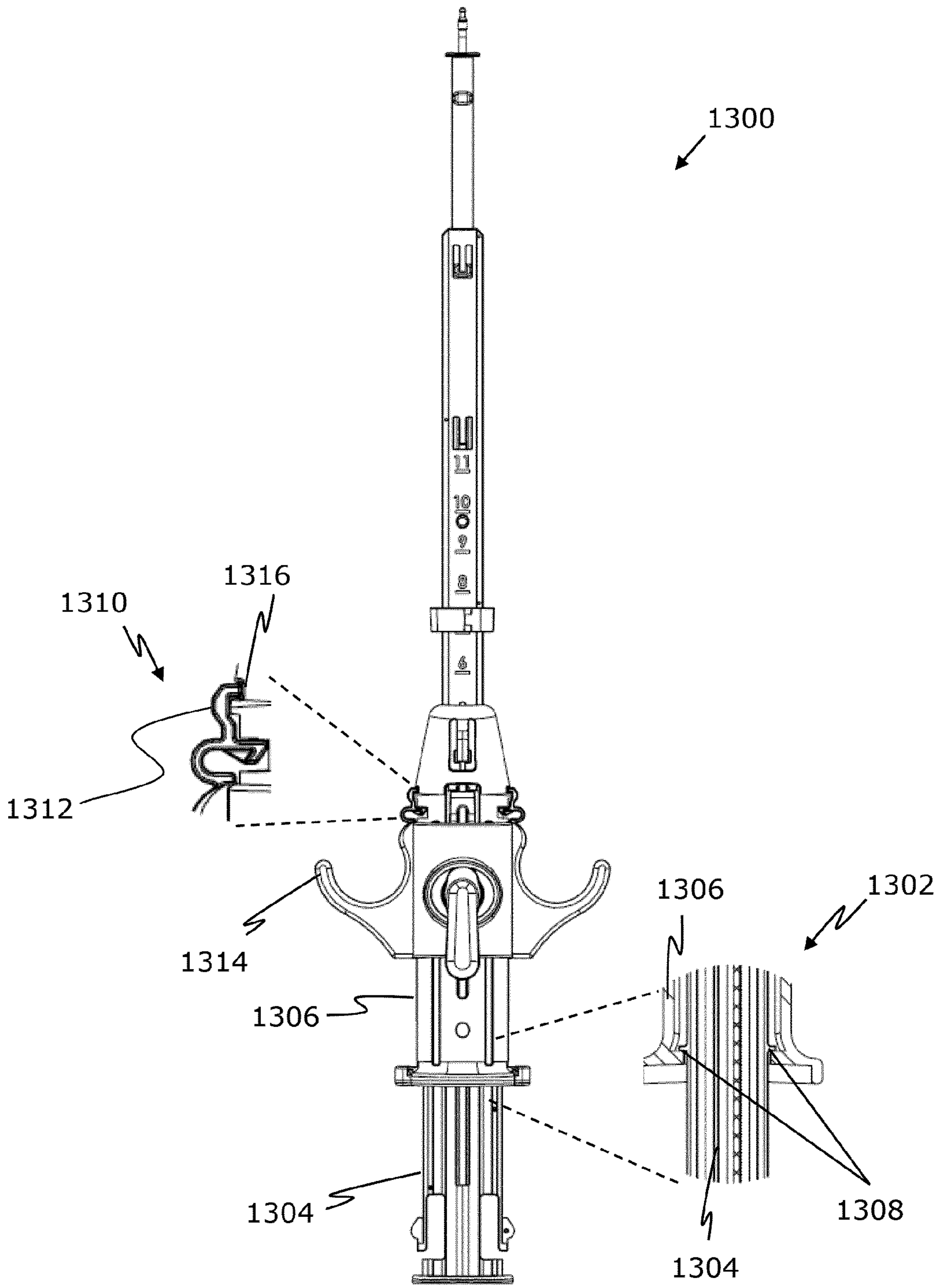
FIGS. 3A-3C illustrate a schematic view of an inserter with enlarged views that depicts internal structure of different sections of the inserter, in accordance with an embodiment of the present disclosure.

FIG. 3A shows a schematic view of an inserter 1300 with an enlarged view of a first section 1302 of the inserter 1300 to depict a piston 1304 that is movably arranged inside a handle body 1306, in accordance with an embodiment of the present disclosure. The piston 1304 comprises a means 1308 for preventing the removal of the piston 1304 from inside the handle body 1306. Further, shown is an enlarged view of a second section 1310 of the inserter 1300 to depict a first hook 1312 of a finger holder 1314 that is locked in a first recess 1316 of the handle body 1306, and which are opened during the insertion process, when the piston is moved towards the distal end of the handle body, for a first part of the movement.

Figure 3B:
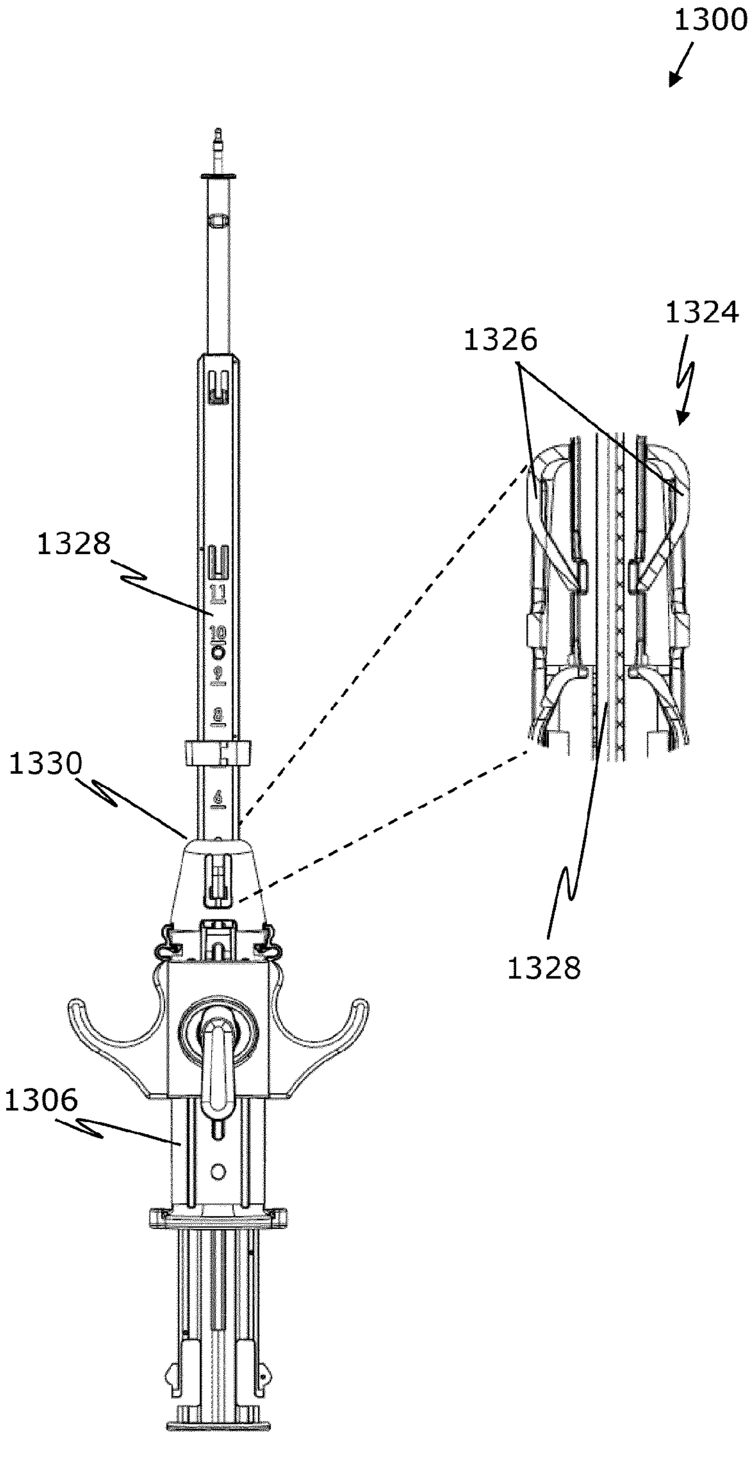

FIG. 3B shows a schematic view of the inserter 1300 with an enlarged view of a fourth section 1324 of the inserter 1300 to depict clamps 1326 that secures a measurement tube 1328, in accordance with an embodiment of the present disclosure. The clamps 1326 secures the measurement tube 1328 in such a manner that the measurement tube 1328 is movably attached inside a distal end 1330 of the handle body 1306. The clamps are opened by the piston towards the end of the insertion, when the IUS is fully inside the uterus and the locking parts are locked together.

Figure 3C:
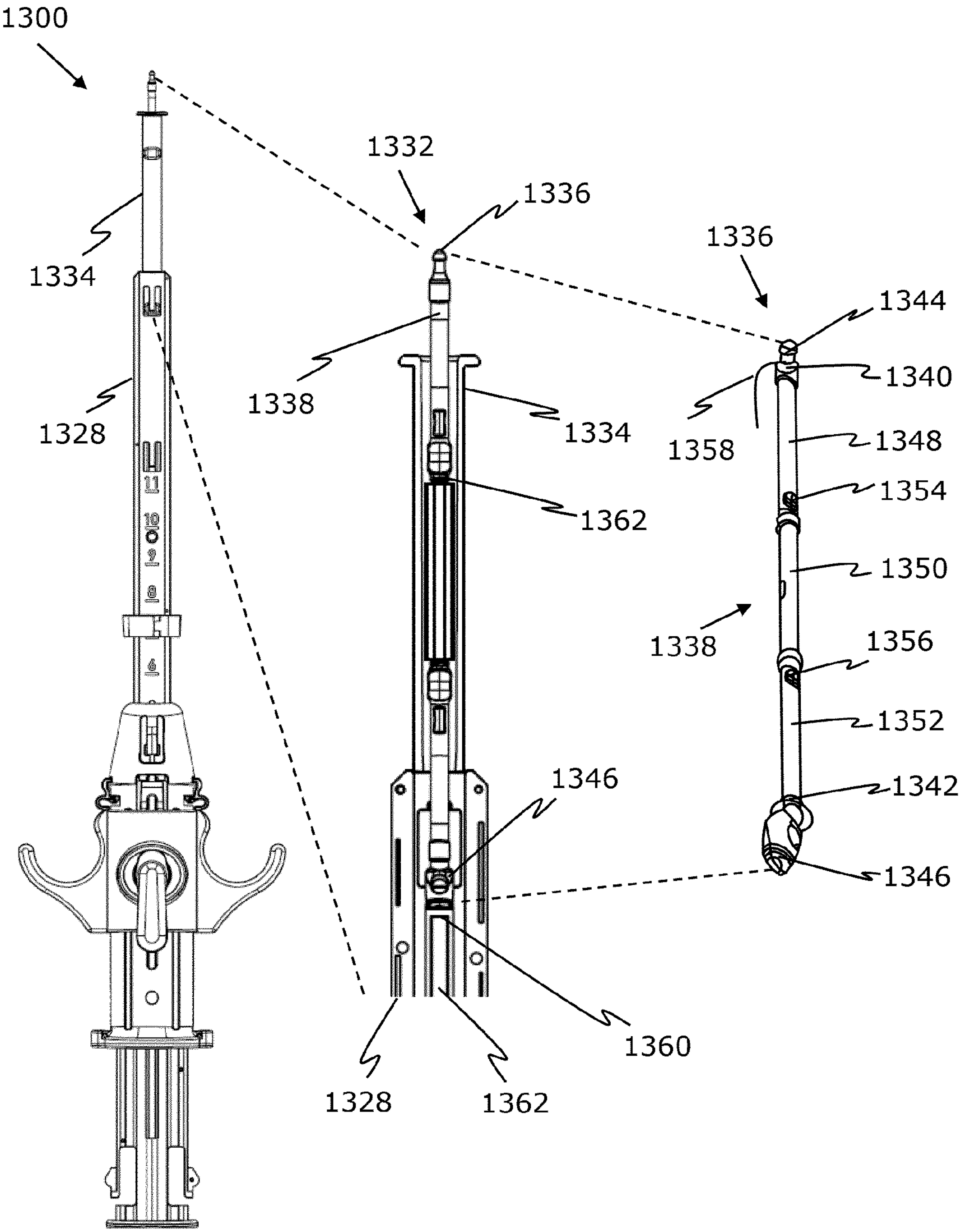

FIG. 3C shows a schematic view of an inserter 1300 with an enlarged view of a fifth section 1332 of the inserter 1300 to depict an arrangement of a tip cover 1334 within the measurement tube 1328. In the fifth section 1332, an IUS 1336 is shown preloaded in the inserter 1300 in such a manner that a small part of a frame 1338 of the IUS 1336 protrudes from the inserter 1300, and the rest of the frame 1338 is surrounded and protected by the tip cover 1334. Further, shown is an enlarged view of the IUS 1336. The frame 1338 of the IUS 1336 has a first end 1340 and a second end 1342. The frame 1338 is straightened and stretched when loaded in the inserter 1300 before inserting the IUS 1336 into the uterus. The first end 1340 of the frame 1338 comprises a first locking part 1344 and the second end 1342 of the frame 1338 comprises a second locking part 1346. In this embodiment, the first locking part 1344 is a pin and the second locking part 1346 is a loop. The IUS 1336 further comprises a pharmaceutically active agent arranged in the frame 1338. The frame 1338 further comprises a first frame segment 1348, a second frame segment 1350 and a third frame segment 1352. The first frame segment 1348 and the second frame segment 1350 are connected with each other via a first bending segment 1354. The second frame segment 1350 and third frame segment 1352 are connected with each other via a second bending segment 1356. A removal thread 1358 is attached to an opening in the first locking part 1344. In the fifth section 1332, there is further shown a distal end 1360 of a plunger 1362 that is configured to cooperate with the second locking part 1346. The plunger 1362 is hollow so as to allow the removal thread 1358 of the IUS 1336 to pass through the plunger 1362.

Figure 4A:
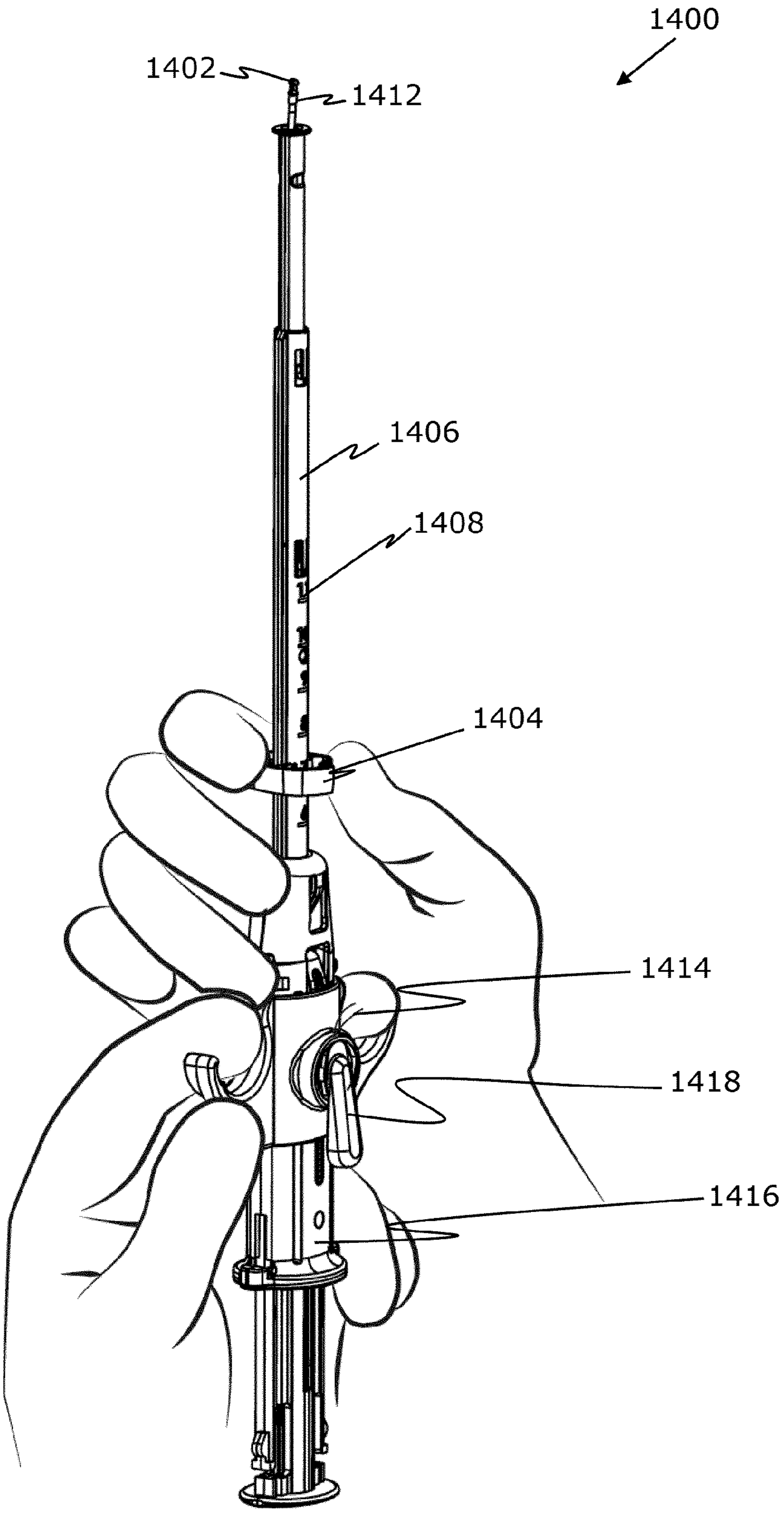
FIGS. 4A-4I illustrate different views of an inserter depicting various operational stages to position an IUS into a uterus, in accordance with various embodiments of the present disclosure.

FIGS. 4A-4H illustrate different views of an inserter 1400 depicting various operational stages to position an IUS 1402 into a uterus, in accordance with an embodiment of the present disclosure. With reference to FIG. 4A, there is shown an adjustment of a flange 1404 on a measurement tube 1406 of the inserter 1400, in accordance with an embodiment of the present disclosure. The flange 1404 is manually moved at a specified position on the measurement tube 1406 with the help of insertion depth indicators 1408 on the outer surface of the measurement tube 1406. The specified position refers to the length of the uterine cavity plus the length of the cervical canal measured previously during uterine sounding. The flange 1404 once set does not move during the insertion process of the IUS 1402. Further, shown is a part of a frame 1412 of the IUS 1402 that is outside the inserter 1400 in a preloaded state. Moreover, in the preloaded state, removal thread 1414 is coupled to one end (i.e. a first end) of the frame 1412, and passes through the inserter 1400 and a portion of the removal thread 1414 emerges from a handle body 1416 of the inserter 1400. A rotatable knob 1418 is arranged in a first position to lock the removal thread 1414 between the handle body 1416 and the rotatable knob 1418.

Figure 4B:
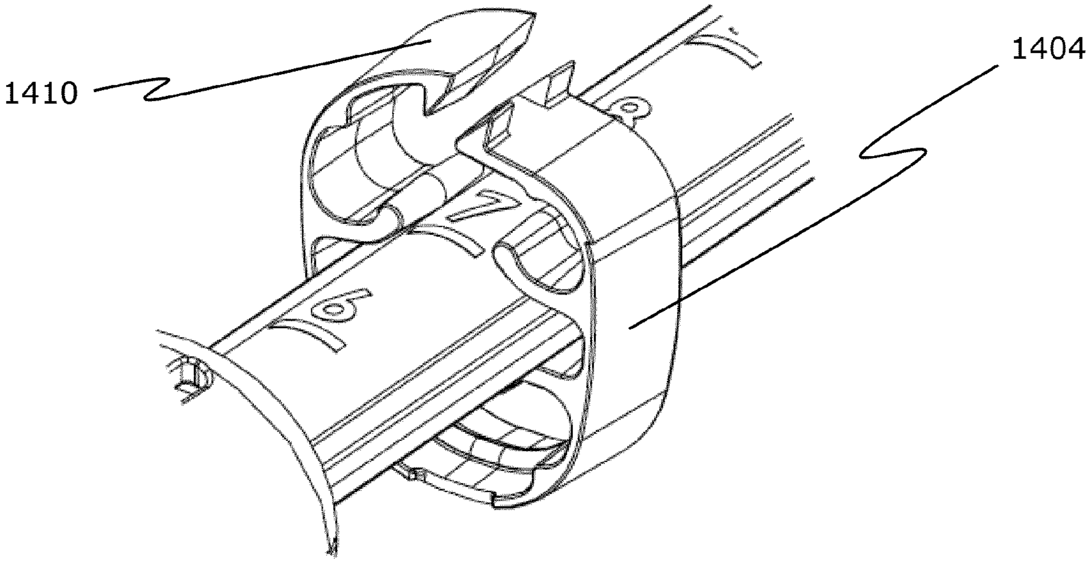
Figure 4C:
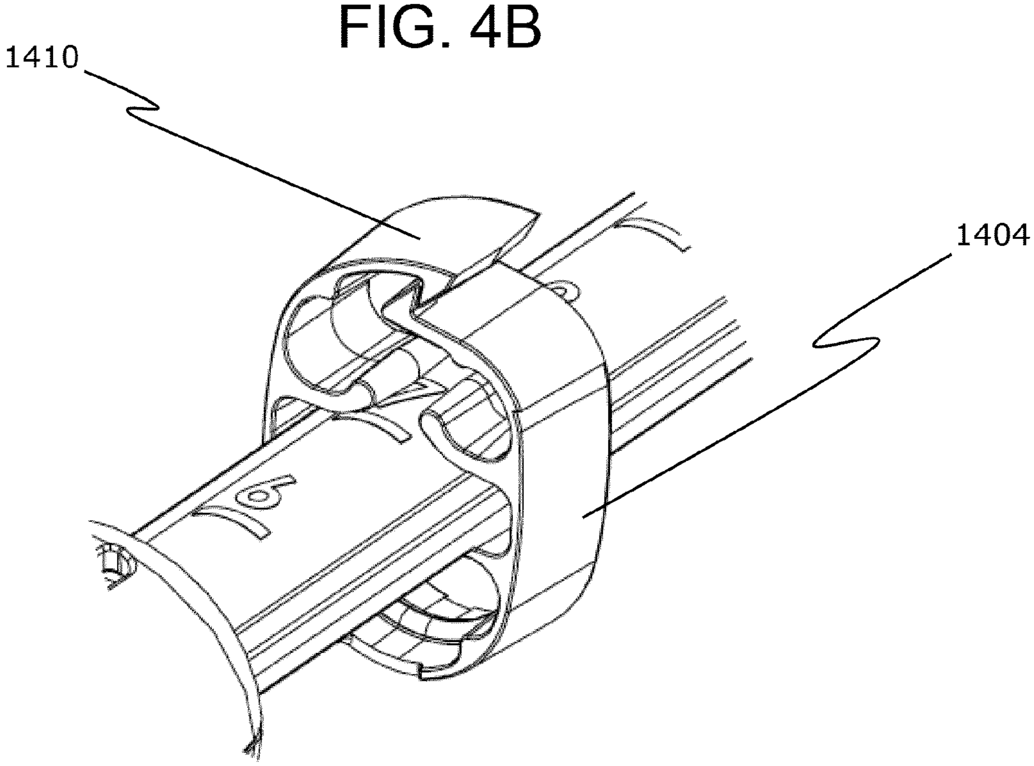

FIGS. 4B and 4C show one embodiment of the flange 1404 in more detail. In this embodiment, the flange 1404 comprises a snap lock 1410 which is originally in an "open" position, where the snap lock 1410 is in an open state, and the flange can be easily moved. Once the flange is in its correct position (on the insertion depth indicators 1408), the snap lock 1410 is closed by pressing the flange, and thus the snap lock will be in a "closed" position.

Figure 4D:
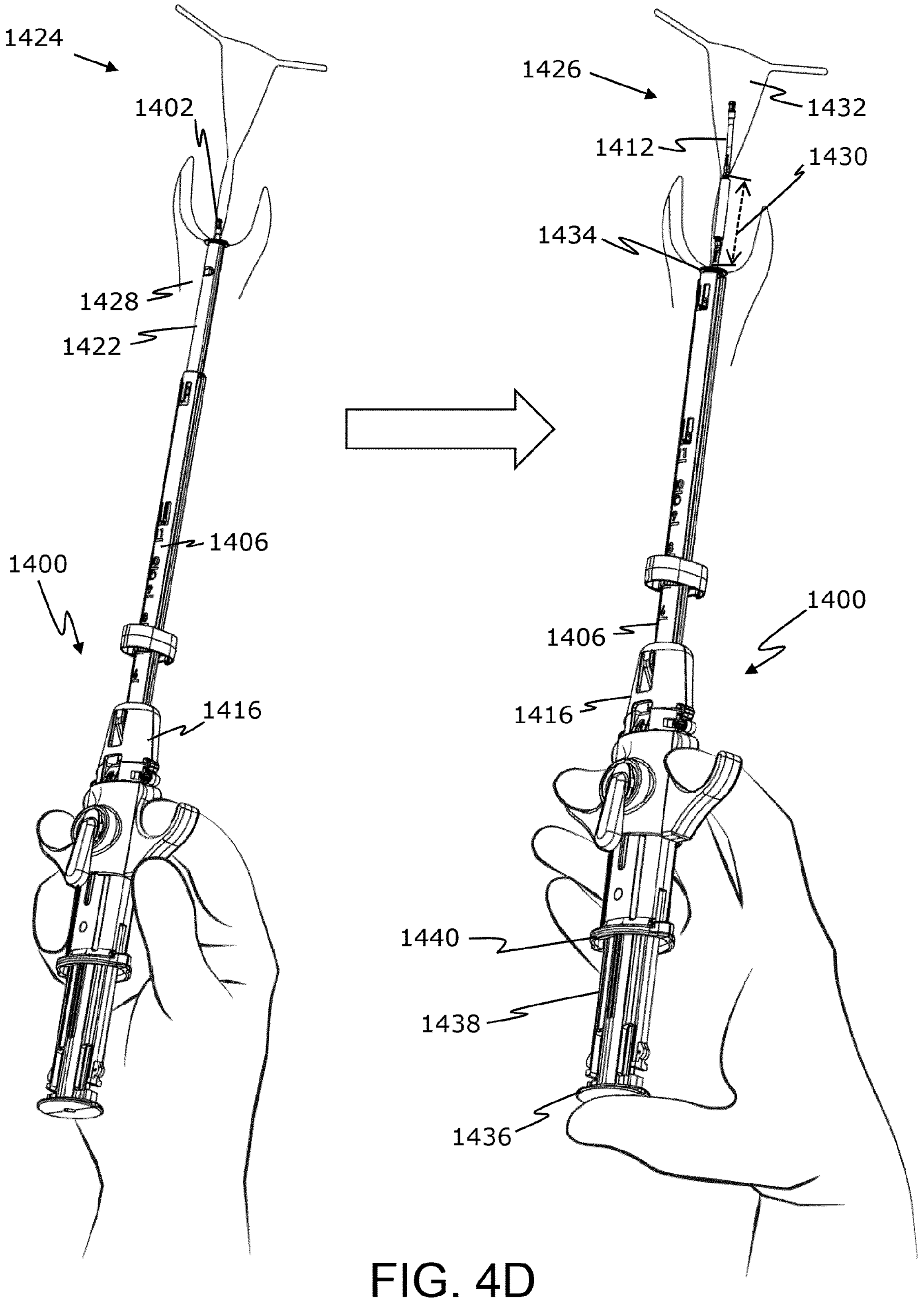

FIG. 4D, shows a first insertion stage of the IUS 1402 using the inserter 1400, in accordance with an embodiment of the present disclosure. In this stage, there is shown a transition from a first state 1424 (on the left) to a second state 1426 (on the right) of the inserter 1400. In the first state 1424 (on the left), a tip cover 1422 is shown in an extended position. The measurement tube 1406 is passed through vagina 1428 towards the cervix. The inserter 1400 is positioned such that the tip cover 1422 reaches the cervix opening and the first end (i.e. the tip) of the IUS 1402 is positioned inside the cervix opening. At this stage, the whole inserter 1400 is gently pushed towards the subject, which makes the tip cover 1422 to move backwards inside the handle body 1416.

In the second state 1426 (on the right), the tip cover is withdrawn inside the handle body 1416, and a part of the frame 1412 is released from the inserter 1400 into the cervical canal 1430 and partially into the uterine cavity 1432. In the second state 1426, further shown is a distal end 1434 of the tip cover that has a round bulbous-like structure to prevent the measurement tube 1406 to enter into the cervical canal 1430. At this stage, a press member 1436 of a piston 1438 is still away from a proximal end 1440 of the handle body 1416 (i.e. the piston 1438 is in an extended state).

Figure 4E:
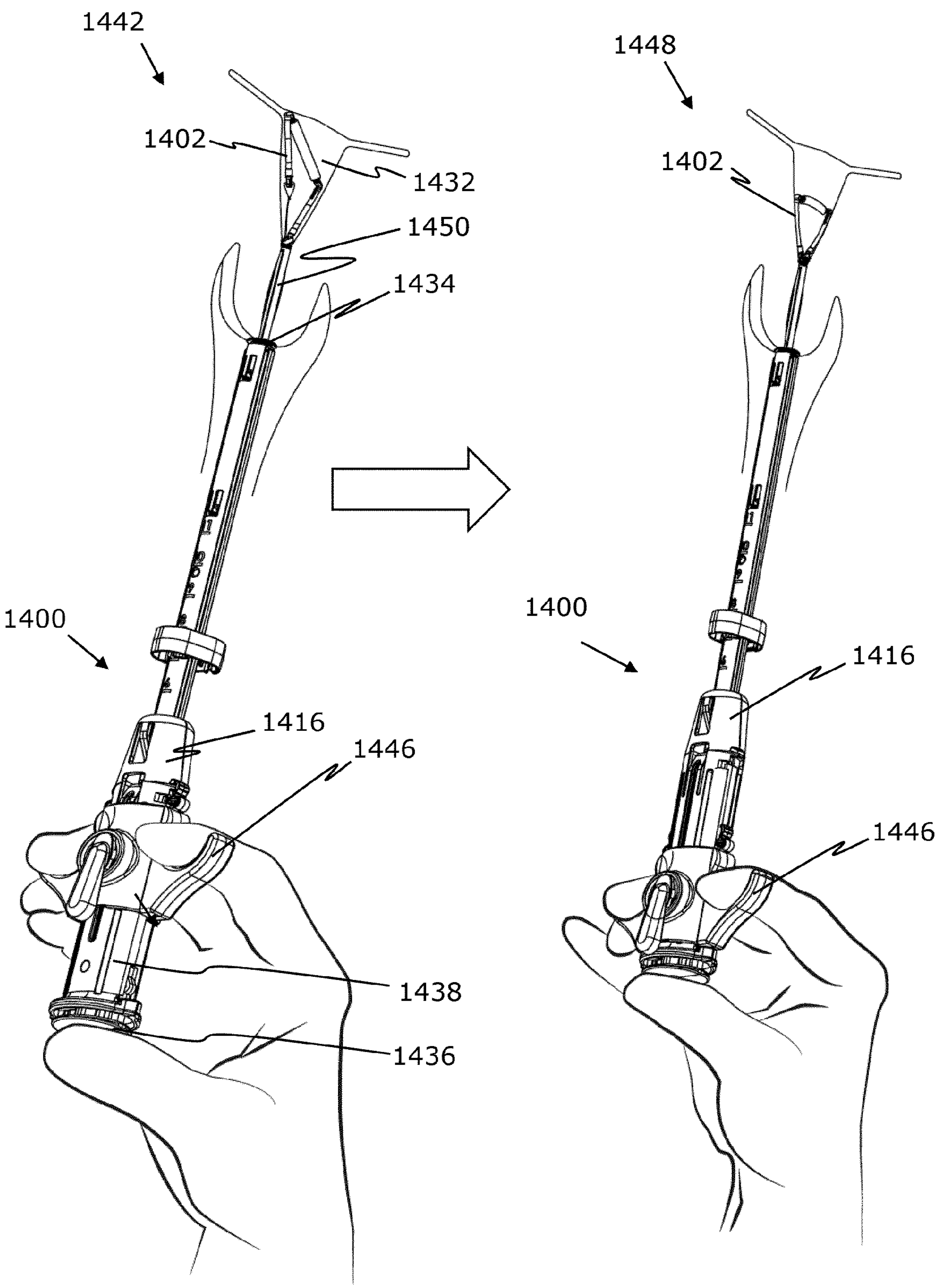

With reference to FIG. 4E, there is shown a second insertion stage of the IUS 1402 using the inserter 1400, in accordance with an embodiment of the present disclosure. In this stage, at operation 1442 (on the left), while maintaining a firm contact of the distal end 1434 of the tip cover (i.e. the tip of the inserter 1400) to the portio of the cervix, the piston 1438 is pressed on the press member 1436 from a proximal end of the piston 1438. A finger holder 1446 is used as a support for fingers (e.g. two fingers in this case) to conveniently press the piston 1438 towards the handle body 1416.

The piston 1438 is pressed from the proximal end until the piston 1438 is completely inside the handle body 1416, and a further movement of the piston 1438 is not allowed (i.e. the movement of the piston 1438 stops). The IUS 1402 starts to exit the inserter 1400 and to form a loop into the uterine cavity 1432. The movement of the piston 1438 moves a plunger 1450 attached to the piston 1438, which in turn pushes an end of the frame and thus more frame is released from the inserter 1400 to form the loop into the uterine cavity 1432.

At operation 1448 (on the right), after the piston has fully entered the handle body 1416, the finger holder 1446 is unlocked and moves towards the proximal end of the handle body 1416. At this stage, the IUS 1402 is outside the inserter 1400, while the IUS 1402 is at the entrance of the uterine cavity 1432. At this stage, the plunger also locks itself inside the inserter 1400 and cannot be moved further by pressing the piston.

Figure 4F:
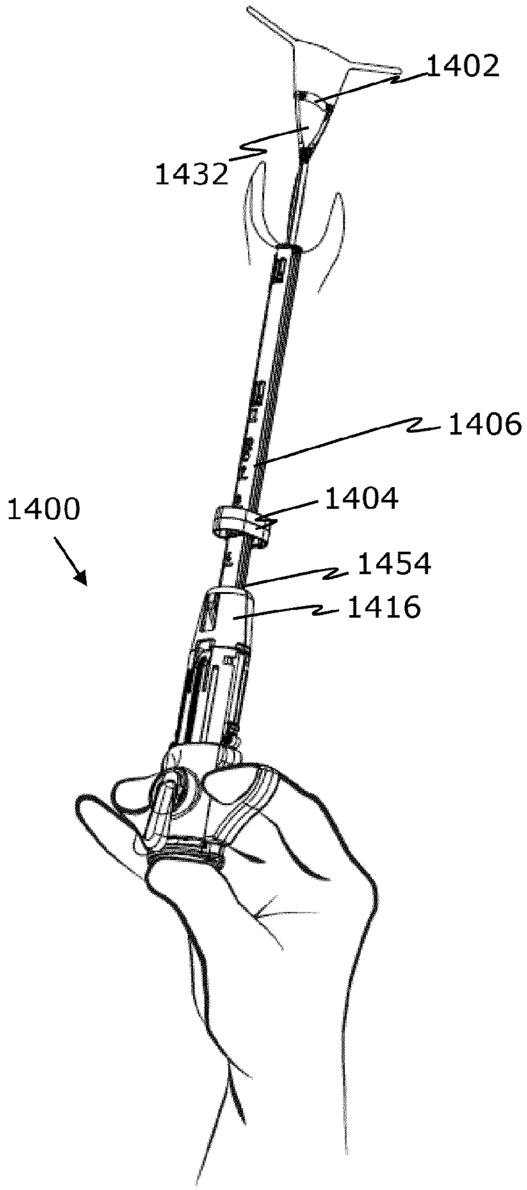

FIG. 4F shows a step where the locking parts of the IUS 1402 lock, while the IUS 1402 is at the entrance of the uterine cavity 1432. The measurement tube 1406 is released and can thus move again.

Figure 4G:
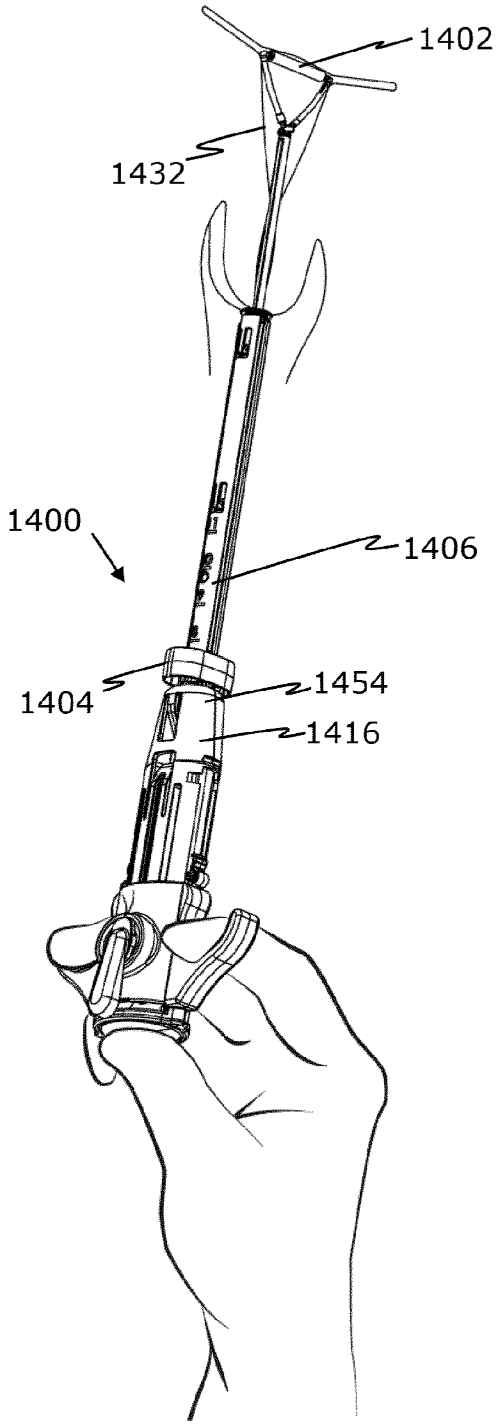

With reference to FIG. 4G, there is shown a third insertion stage of the IUS 1402 using the inserter 1400, in accordance with an embodiment of the present disclosure. In this stage, the inserter 1400 is pushed towards the patient until the flange 1404 meets the handle body 1416 (i.e. a part of the proximal end of the measurement tube 1406 enters inside a distal end 1454 of the handle body 1416). During this stage, the IUS 1402 moves into its fundal position and the whole IUS 1402 is accurately positioned into the uterine cavity 1432.

Figure 4H:
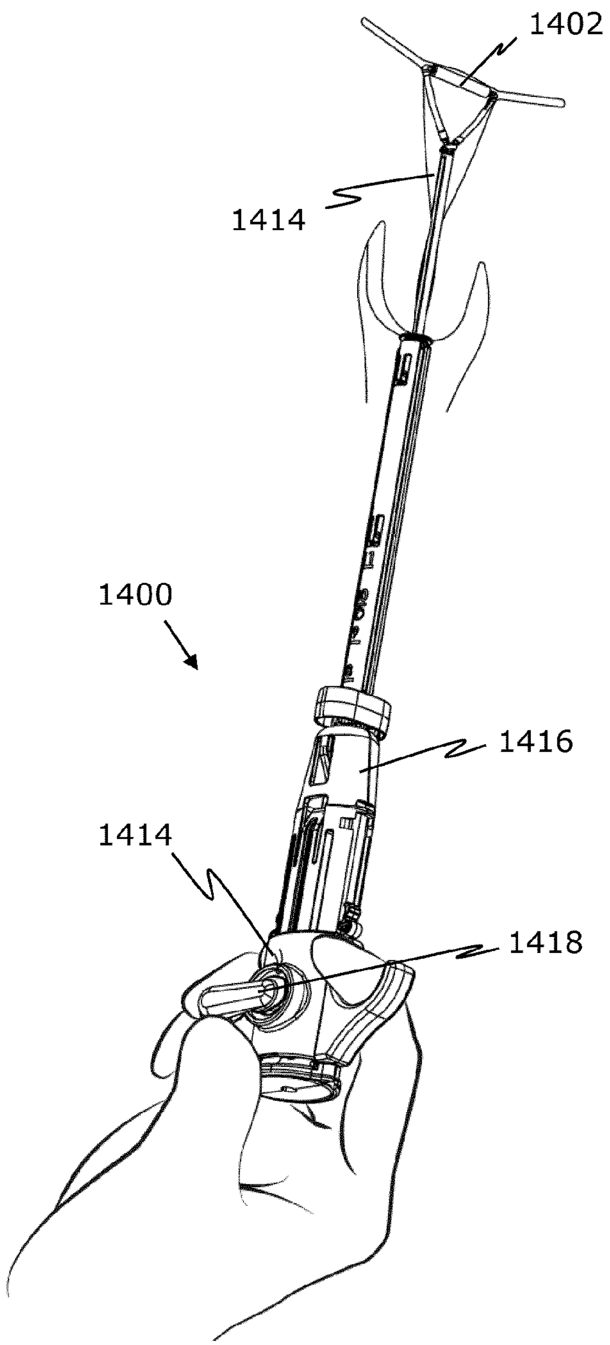

With reference to FIG. 4H, there is shown a release of the removal thread 1414 using the inserter 1400 after the IUS 1402 is deployed in the uterine cavity, in accordance with an embodiment of the present disclosure. In this stage, the removal thread 1414 is released using the rotatable knob 1418. The rotatable knob 1418 is moved to a second position from its initial first position to allow the removal thread 1414 to be moved with respect to the handle body 1416, and finally get released.

Figure 4I:
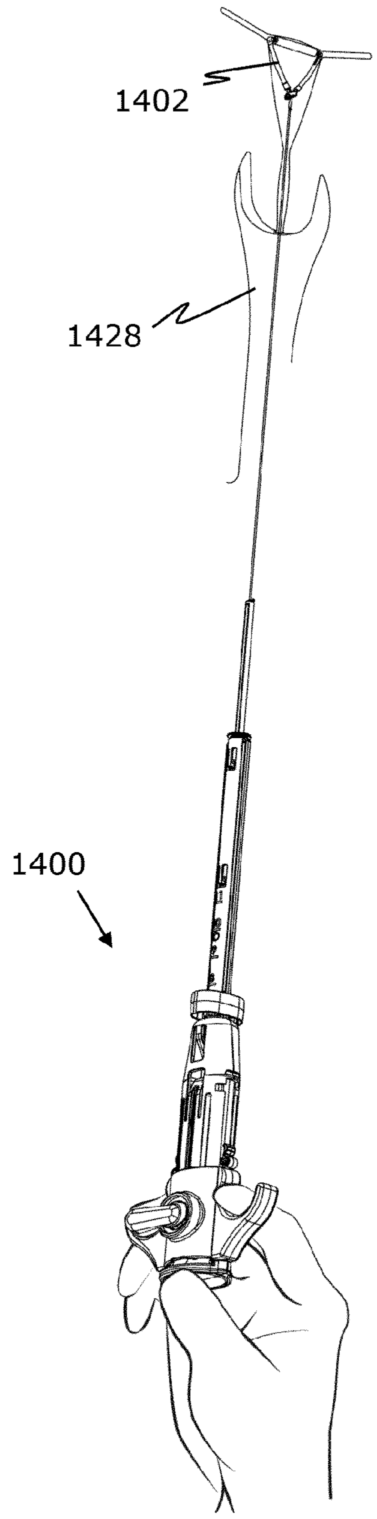

With reference to FIG. 4I, there is shown removal of the inserter 1400 from a subject, in accordance with an embodiment of the present disclosure. The inserter 1400 is pulled out from the vagina 1428 denoting the completion of the insertion process of the IUS 1402 by the inserter 1400.

Figure 5A:
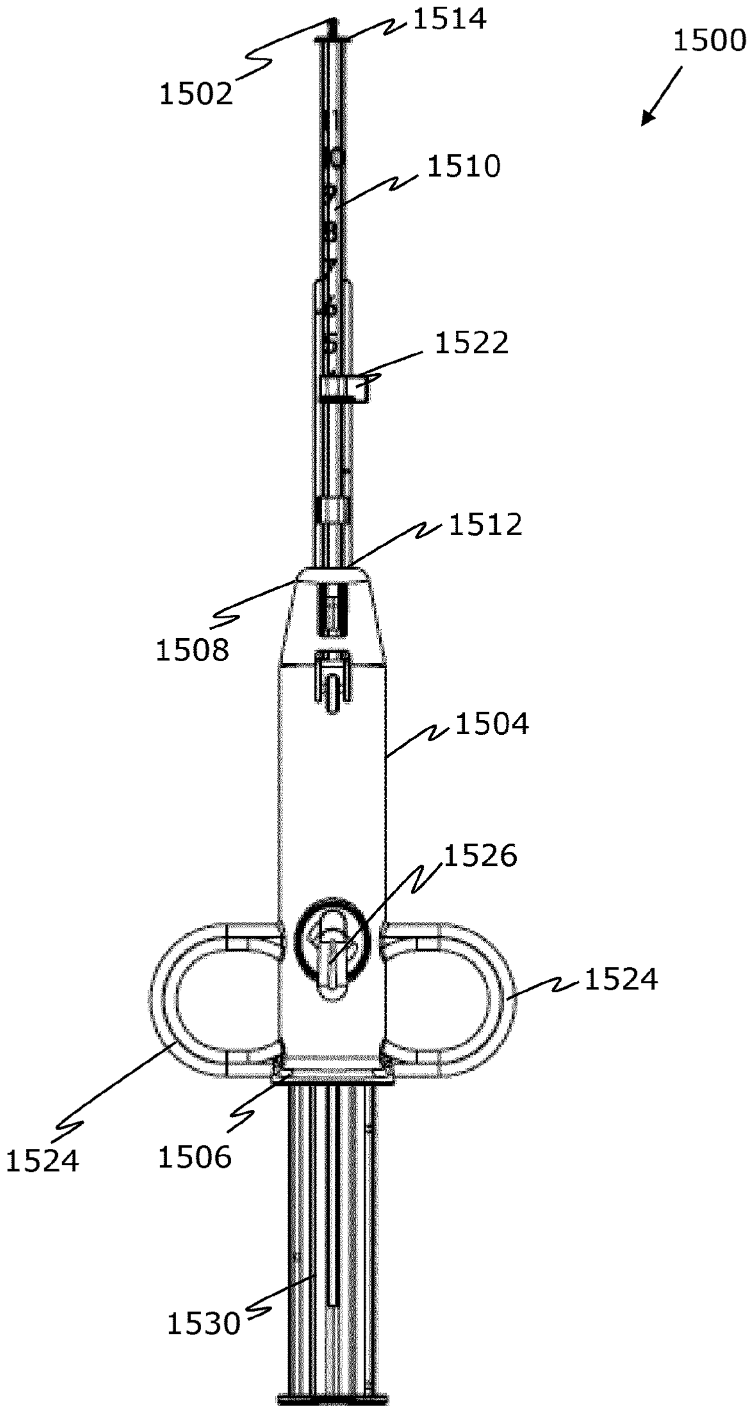
FIGS. 5A and 5B illustrate an inserter in an assembled and unassembled states, respectively, in accordance with another embodiment of the present disclosure.

Referring to FIG. 5A, there is shown a schematic view of an inserter 1500 in an assembled state preloaded with an IUS 1502, in accordance with another embodiment of the present disclosure. The inserter 1500 comprises a handle body 1504 having a proximal end 1506 and a distal end 1508. The inserter 1500 further comprises a measurement tube 1510 having a proximal end 1512 and a distal end 1514. The proximal end 1512 of the measurement tube 1510 is movably attached to the distal end 1508 of the handle body 1504. The inserter 1500 further comprises a flange 1522 movably arranged around the measurement tube 1510. A finger holder 1524 is arranged on the handle body 1504. In this embodiment, the finger holder 1524 is in a ring shape, i.e. in the form of circles extending outwards from diametrically opposite sides of the outer surface of the handle body 1504 at its proximal end 1506. The inserter 1500 further comprises a means 1526 for reversibly locking a removal thread of the IUS 1502. The means 1526 for reversibly locking a removal thread is arranged on the handle body 1504. The inserter 1500 further comprises a piston 1530 that is movably arranged inside the handle body 1504.

Figure 5B:
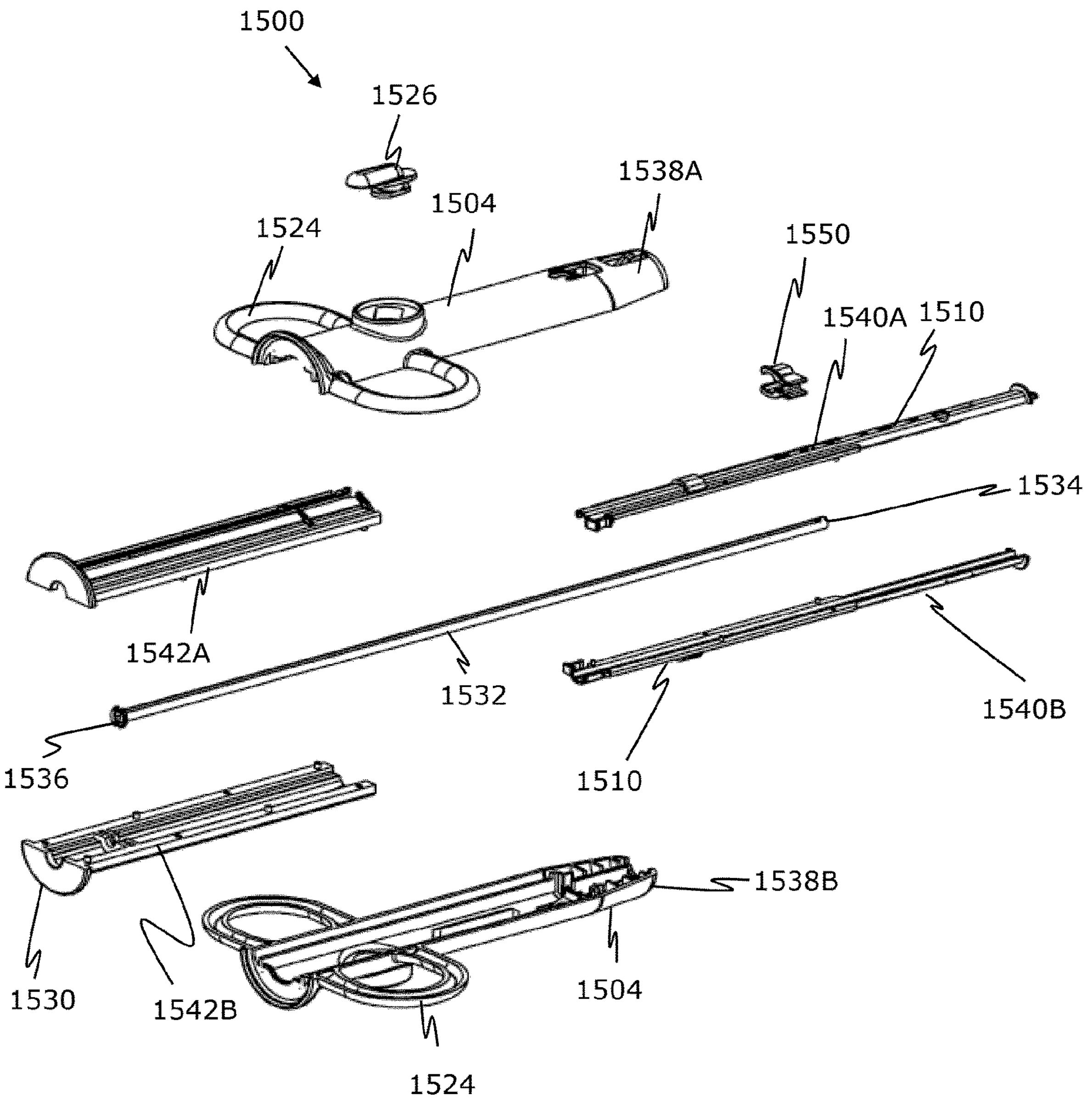

Referring to FIG. 5B, there is shown a perspective view of the inserter 1500 of FIG. 5A in an unassembled state, in accordance with an embodiment of the present disclosure. The inserter 1500 further comprises a plunger 1532 plunger having a distal end 1534 and a proximal end 1536. In the assembled state of the inserter 1500, the plunger 1532 is movably arranged inside the handle body 1504 and the measurement tube 1510. The handle body 1504 has a first cover portion 1538A and a second cover portion 15388. Further, shown is a first part 1540A and a second part 154013 of the measurement tube 1510, and a first part 1542A and a second part 15428 of the piston 1530. Further, shown is the means 1526 for reversibly locking the removal thread of the IUS 1502, as well as a flange 1550.

Figure 6:
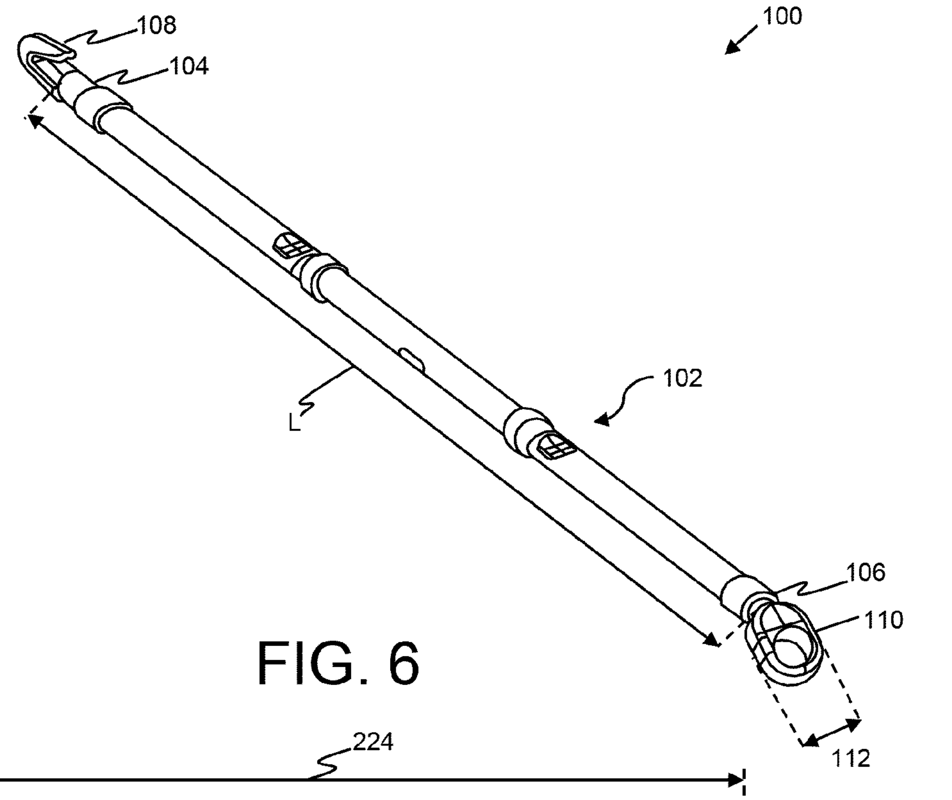
FIG. 6 is a perspective view of an IUS in a loaded configuration, in accordance with an embodiment of the present disclosure.

FIG. 6 shows a perspective view of an IUS 100 in a loaded configuration, in accordance with an embodiment of the present disclosure. As shown, the IUS 100 comprises a frame 102 having a first end 104, a second end 106 and a length L defined as a distance from the first end 104 to the second end 106. The frame 102 is straightened and stretched when loaded in an inserter before inserting the IUS 100 into the uterus. The first end 104 of the frame 102 comprises a first locking part 108 and the second end 106 of the frame 102 comprises a second locking part 110. In this embodiment, the first locking part 108 is a hook and the second locking part 110 is a loop. Further, shown is an outer diameter 112 (i.e. the largest outer diameter) of the IUS 100. The IUS 100 further comprises a pharmaceutically active agent arranged in the frame 102.

Figure 7:
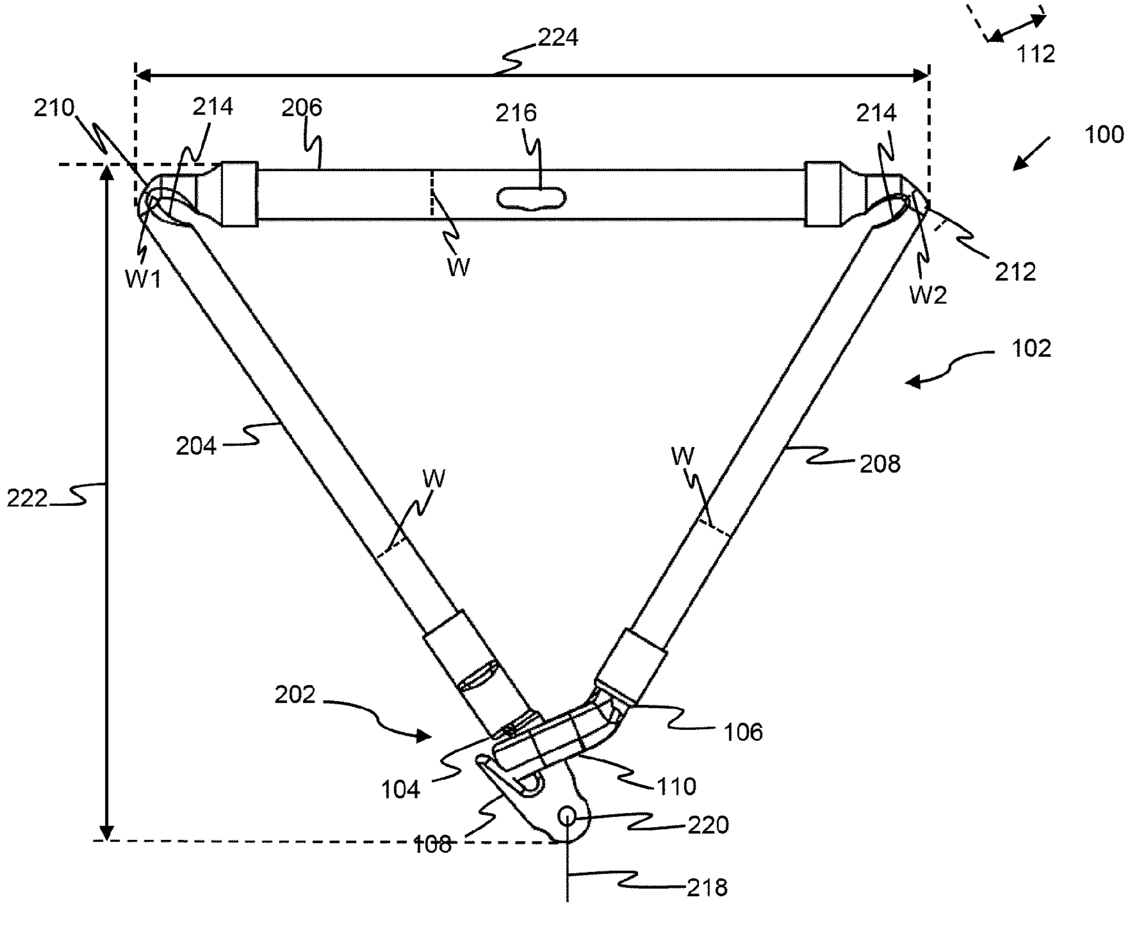
FIG. 7 is a schematic view of the IUS of FIG. 6, in accordance with an embodiment of the present disclosure.

Now referring to FIG. 7, there is shown a schematic view of the IUS 100 of FIG. 6, in accordance with an embodiment of the present disclosure. In this embodiment, the frame 102 of the IUS 100 is a triangular-shaped frame. The first locking part 108 at the first end 104 of the frame 102 and the second locking part 110 at the second end 106 of the frame 102 are arranged to form a lock 202 in the deployed state in the uterus.

The frame 102 further comprises a first frame segment 204, a second frame segment 206 and a third frame segment 208. The first frame segment 204 and second frame segment 206 are connected with each other via a first bending segment 210. The second frame segment 206 and third frame segment 208 are connected with each other via a second bending segment 212. The width W of the first frame segment 204, the second frame segment 206 and the third frame segment 208 is the same as the width of the frame 102. Further, shown is the first bending segment 210 having a first width W1 and the second bending segment 212 having a second width W2. In this embodiment, the cross-section of the frame 102 at the first bending segment 210 and at the second bending segment 212 has an essentially concave shape 214. The first width W1 and the second width W2 is the smallest dimension of the cross-section of the frame 102. In this embodiment, the first width W1 is essentially identical to the second width W2, and each of the first width W1 and the second width W2 is about 25% of the width W. The smaller cross-section (i.e. a localized thinning) at the first bending segment 210 and the second bending segment 212 as compared to the other portions of the frame 102 facilitate bending of the frame 102 into the triangular-shape. The frame 102 further comprises a bending point 216 that facilitates removal of the IUS 100 when required.

The IUS 100 further comprises a removal thread 218 attached to the first end 104 of the frame 102. Specifically, the removal thread 218 is coupled to an opening 220 in the first locking part 108 at the first end 104 of the frame 102. The removal thread 218 is configured to guide the first locking part 108 towards the second locking part 110. Further, shown is a length 222 and a width 224 of a frame 102 of the triangular-shaped IUS 100 in the deployed state in the uterus.

Figure 8:
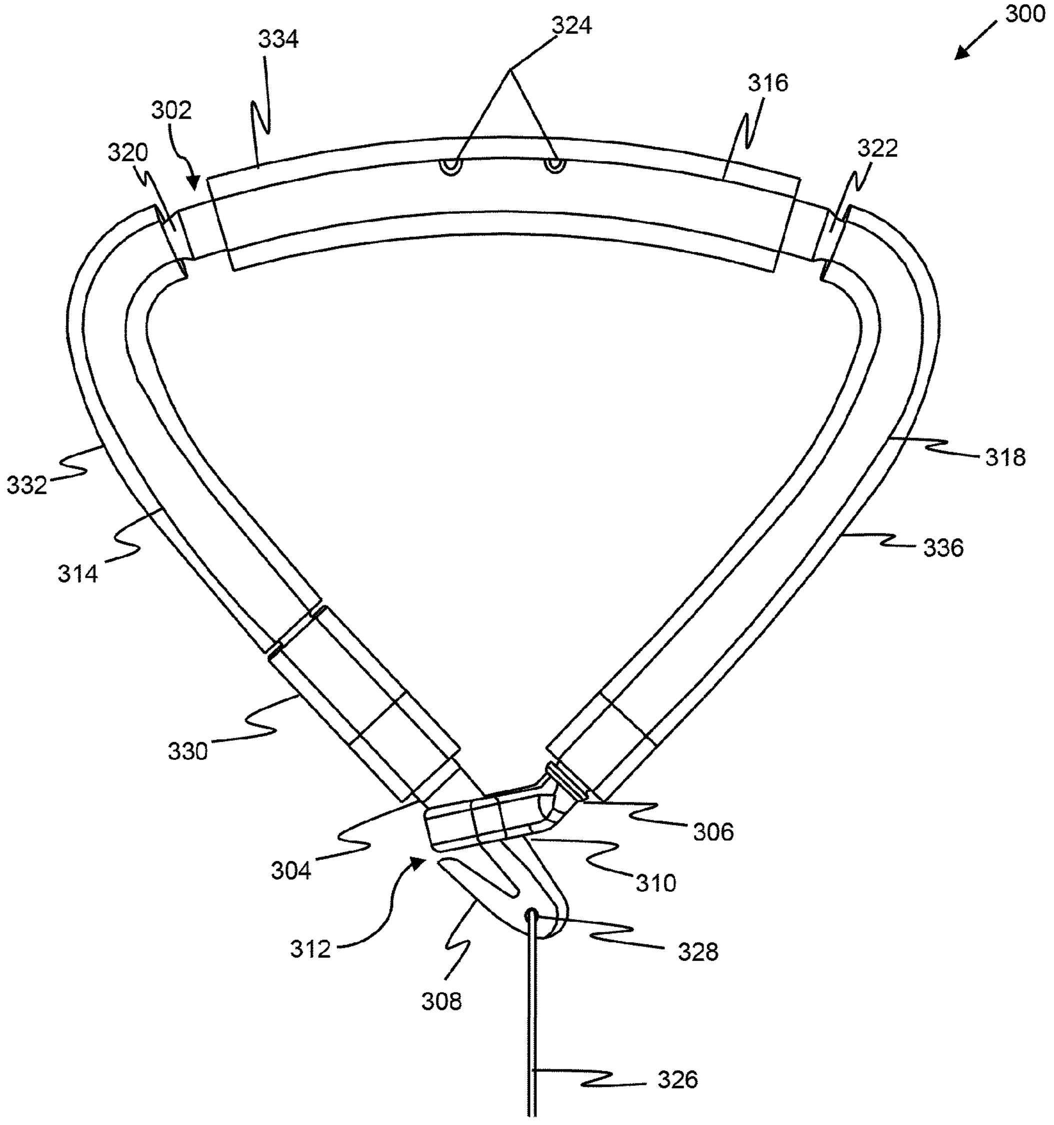
FIG. 8 is a schematic view of an IUS, in accordance with another embodiment of the present disclosure.

Now referring to FIG. 8, shown is a schematic view of an IUS 300, in accordance with another embodiment of the present disclosure. The IUS 300 comprises a frame 302 having a first end 304 and a second end 306. In this embodiment, the frame 302 is a triangular-shaped frame. The first end 304 of the frame 302 comprises a first locking part 308 and the second end 306 of the frame 302 comprises a second locking part 310. The first locking part 308 and the second locking part 310 are arranged to form a lock 312. The first locking part 308 is a hook and the second locking part 310 is a loop, and the hook is arranged to be irremovably inserted into the loop.

The frame 302 further comprises a first frame segment 314, a second frame segment 316 and a third frame segment 318. The first frame segment 314 is connected to the second frame segment 316 via a first bending segment 320. Similarly, the second frame segment 316 is connected to the third frame segment 318 via a second bending segment 322. In this embodiment, the frame 302 further comprises two bending points 324 allowing the IUS 300 to be removed. The region between the two bending points 324 is a weaker part of the frame 302 as compared to other parts of the frame 302.

The IUS 300 further comprises a removal thread 326 attached to the first end 304 of the frame 302. The removal thread 326 is received in an opening 328 provided in the first locking part 308. The removal thread 326 is configured to guide the first locking part 308 towards the second locking part 310. The IUS 300 further comprises four capsules, a first capsule 330, a second capsule 332, a third capsule 334 and a fourth capsule 336. The first capsule 330 is shorter in length as compared to other capsules 332, 334, and 336. The capsules 330, 332, 334 and 336 comprise same or different pharmaceutically active agents.

Figure 9A:
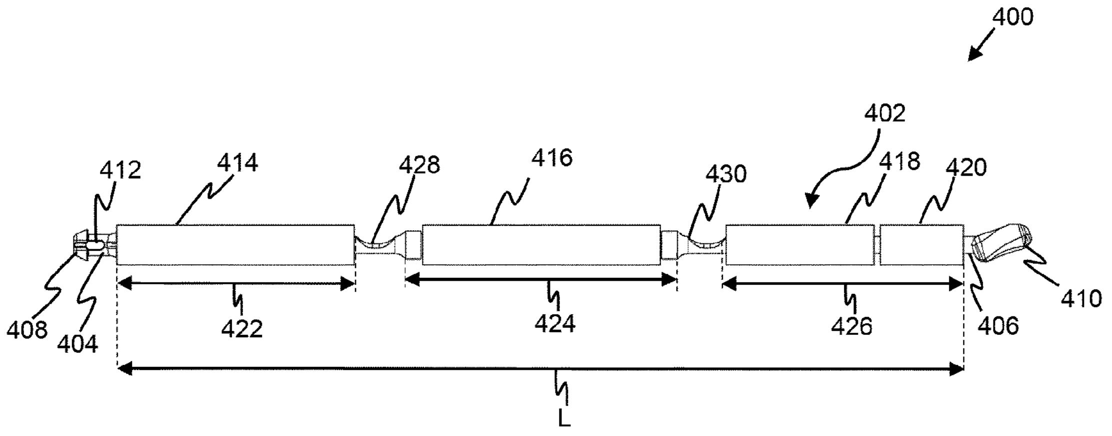
FIG. 9A is a schematic view of an IUS in a loaded configuration, in accordance with yet another embodiment of the present disclosure.

Now referring to FIG. 9A, shown is a schematic view of an IUS 400 in a loaded configuration, in accordance with yet another embodiment of the present disclosure. As shown, the IUS 400 comprises a frame 402 having a first end 404 and a second end 406, and a length L is defined as a distance from the first end 404 to the second end 406. The frame 402 is straightened and stretched when loaded in an inserter (i.e. in the loaded configuration) before inserting the IUS 400 into the uterus. The first end 404 of the frame 402 comprises a first locking part 408 and the second end 406 of the frame 402 comprises a second locking part 410. In this embodiment, the first locking part 408 is a pin and the second locking part 410 is a loop. The first locking part 408 and the second locking part 410 have complementary structures to enable the pin to be irremovably inserted into the loop. The first locking part 408 of the IUS 400 comprises an opening 412 for receiving a removal thread.

The frame 402 further comprises a first capsule 414, a second capsule 416, a third capsule 418, and a fourth capsule 420. The first capsule 414 and the second capsule 416 are arranged to surround a first frame segment 422 and a second frame segment 424 respectively. The third capsule 418 and the fourth capsule 420 are arranged to surround a third frame segment 426 of the frame 402. Further, shown is a first bending segment 428 and a second bending segment 430. The first frame segment 422 is connected to the second frame segment 424 via the first bending segment 428, and the second frame segment 424 is connected to the third frame segment 426 via the second bending segment 430.

Figure 9B:
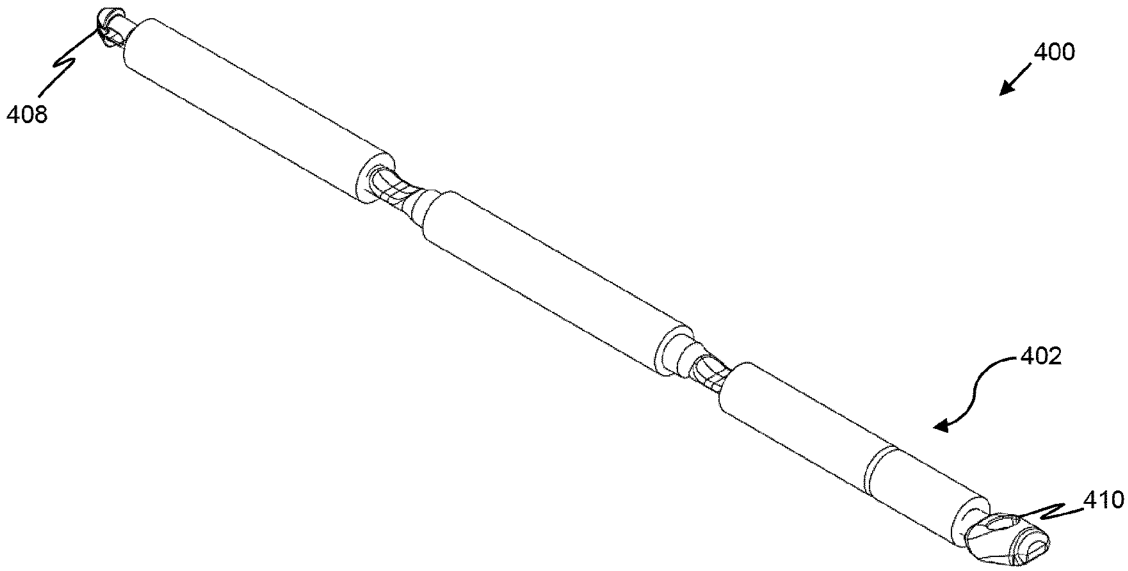
FIG. 9B is a perspective view of the IUS of FIG. 9A in a loaded configuration, in accordance with an embodiment of the present disclosure.

Now referring to FIG. 9B, shown is a perspective view of the IUS 400 of FIG. 9A, in accordance with an embodiment of the present disclosure. As shown, the first locking part 408 is a pin and the second locking part 410 is a loop, i.e. having geometrically complementing structures, such that the pin substantially engages in the loop in the deployed state of the IUS 400 in the uterus.

Figure 9C:
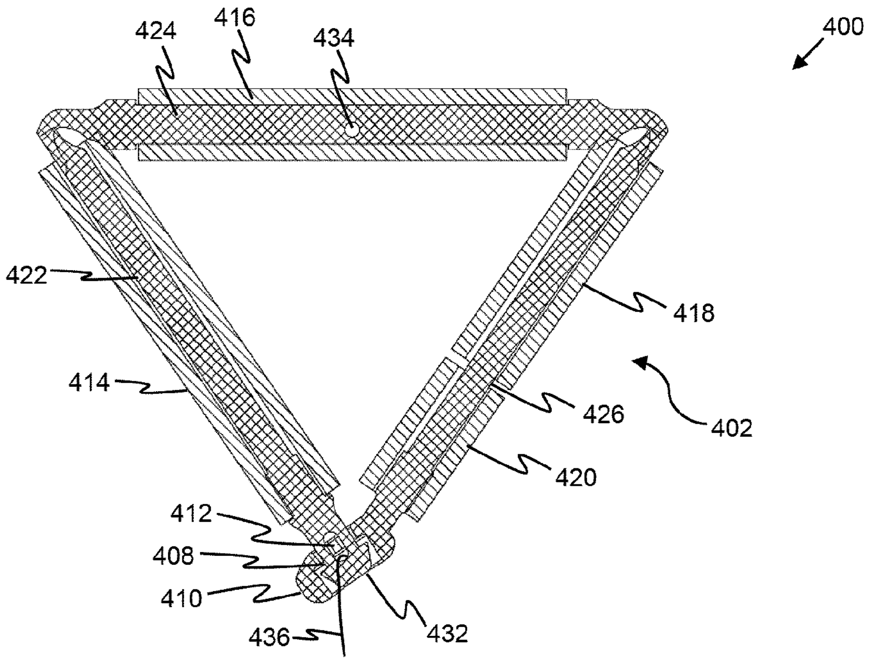
FIG. 9C is a cross-sectional view of the IUS of FIG. 9A in a deployed state, in accordance with an embodiment of the present disclosure.

Now referring to FIG. 9C, shown is a schematic cross-sectional view of the IUS 400 in a deployed state, in accordance with an embodiment of the present disclosure. In the deployed state, the frame 402 of the IUS 400 attains a triangular-shape when the first locking part 408 and the second locking part 410 engages to form a lock 432. The frame 402 further comprises a bending point 434 allowing the IUS 400 to be removed. In this embodiment, the bending point 434 is provided in a middle section of the second bending segment 424, and is a weaker part as compared to the other parts of the frame 402. Further, shown is the first capsule 414 arranged to surround the first frame segment 422, the second capsule 416 arranged to surround the second frame segment 424, the third capsule 418 arranged to surround a part of a third frame segment 426 and a fourth capsule 420 arranged to surround another part of the third frame segment 426 of the frame 402 respectively. The first locking part 408 comprises an opening 412 for receiving a removal thread 436. The removal thread 436 guides the first locking part 408 to come in contact to the second locking part 410 and further to engage the first locking part 408 with the second locking part 410 to provide the desired triangular-shape to the frame 402 in the uterus in the deployed state.

Figure 9D:
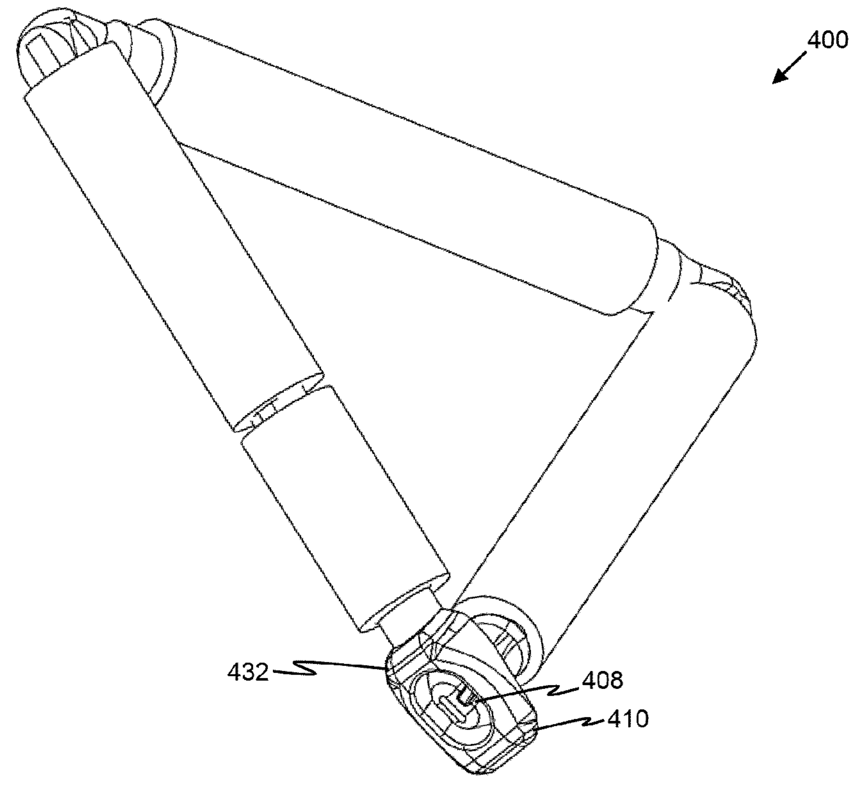
FIG. 9D is a perspective view of the IUS of FIG. 9A in a deployed state, in accordance with various embodiments of the present disclosure.

Now referring to FIG. 9D, shown is a perspective view of the IUS 400 of the FIG. 9C in a deployed state, in accordance with an embodiment of the present disclosure. As shown, the first locking part 408 and the second locking part 410 have geometrically complementing structures, such that the first locking part 408 substantially engages in the second locking part 410 and form the lock 432 in the deployed state in the uterus.

Figure 10:
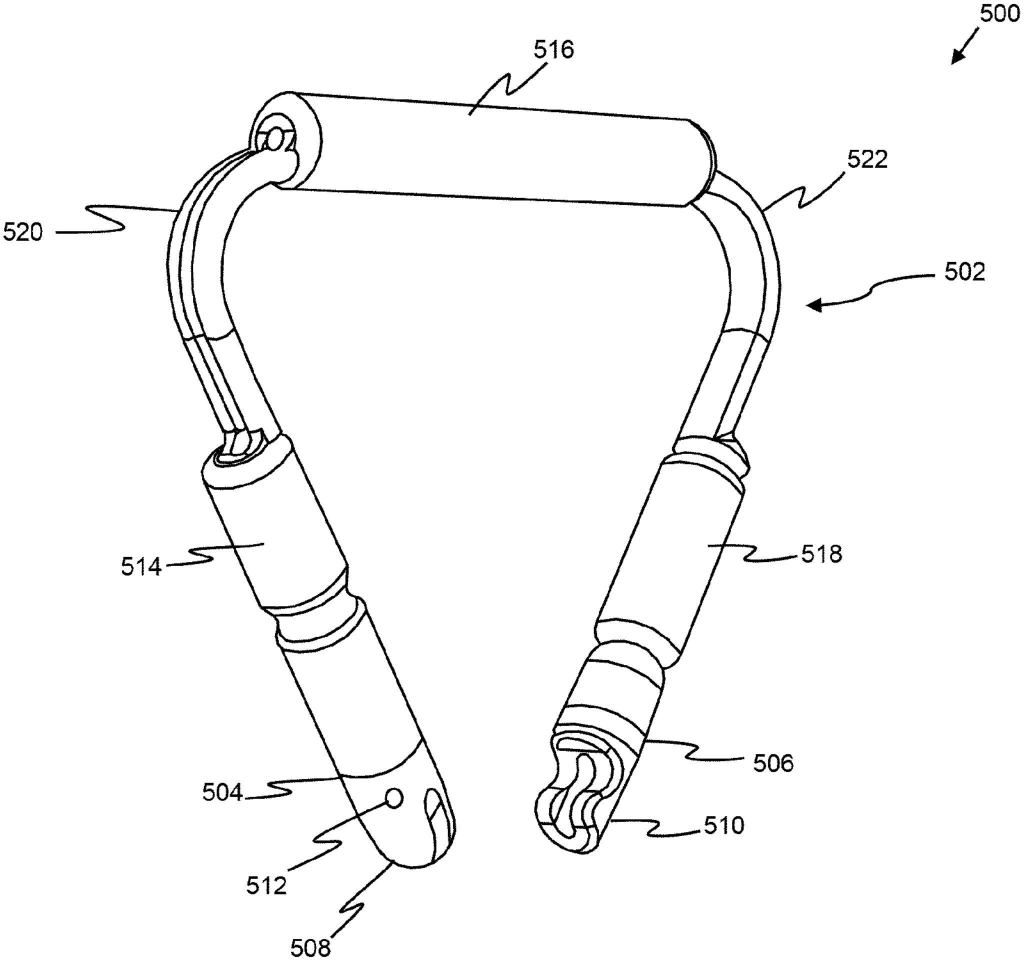
FIG. 10 is a perspective view of an IUS, in accordance with still another embodiment of the present disclosure.

FIG. 10 shows a schematic view of an IUS 500, in accordance with still another embodiment of the present disclosure. The IUS 500 comprises a frame 502 having a first end 504 and a second end 506. The first end 504 of the frame 502 comprises a first locking part 508 and the second end 506 of the frame 502 comprises a second locking part 510. The first locking part 508 and the second locking part 510 have geometrically complementing structures in a clamp and column arrangement to allow the first locking part 508 to be locked to the second locking part 510. The first locking part 508 comprises an opening 512 for receiving a removal thread. The frame 502 further comprises a first capsule 514, a second capsule 516 and a third capsule 518 that are spaced apart and arranged to surround a part of the frame 502. In this embodiment, the frame 502 has a rounded rectangular tube-like cross-section. In the deployed state in the uterus, the frame 502 bends at two bending segments 520 and 522 that are devoid of the capsules, i.e. the first capsule 514, the second capsule 516, and the third capsule 518.

Figure 11A:
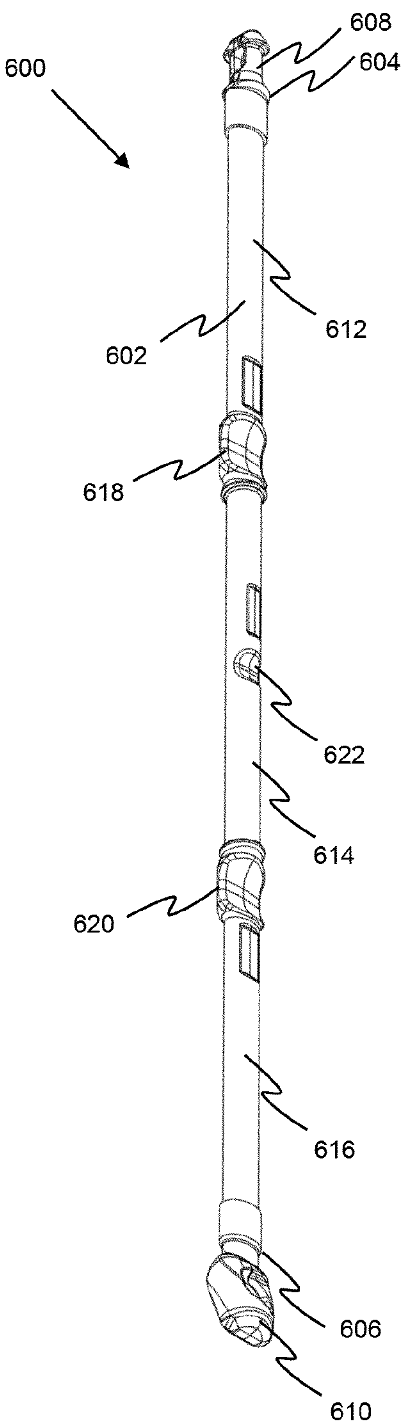
FIGS. 11A-11D are schematic illustrations of a frame and of an IUS according to an embodiment.

FIGS. 11A-11D are schematic illustrations of a frame of an IUS and of the IUS according to an embodiment, as well as show how the IUS is locked into shape. Indeed, FIG. 11A shows the frame 602 of the IUS. The Figure also shows a first end 604 of the frame and a second end 606 of the frame. The first end 604 of the frame 602 comprises a first locking part 608 and the second end 606 of the frame 602 comprises a second locking part 610. In this embodiment, the first locking part 608 is a knob and the second locking part 610 is a loop.

The frame 602 further comprises a first frame segment 612, a second frame segment 614 and a third frame segment 616. The first frame segment 612 and second frame segment 614 are connected with each other via a first bending segment 618. The second frame segment 614 and third frame segment 616 are connected with each other via a second bending segment 620. The width of the first frame segment 612, the second frame segment 614 and the third frame segment 616 is smaller than the width of the locking parts 608 and 610. In this embodiment, the cross-section of the frame 602 at the first bending segment 618 and at the second bending segment 620 has an essentially concave shape. Moreover, the width of the bending segments is larger than the width of the frame segments. The frame 602 further comprises a bending point 622 that facilitates removal of the IUS 600 when required.

Figure 11B:
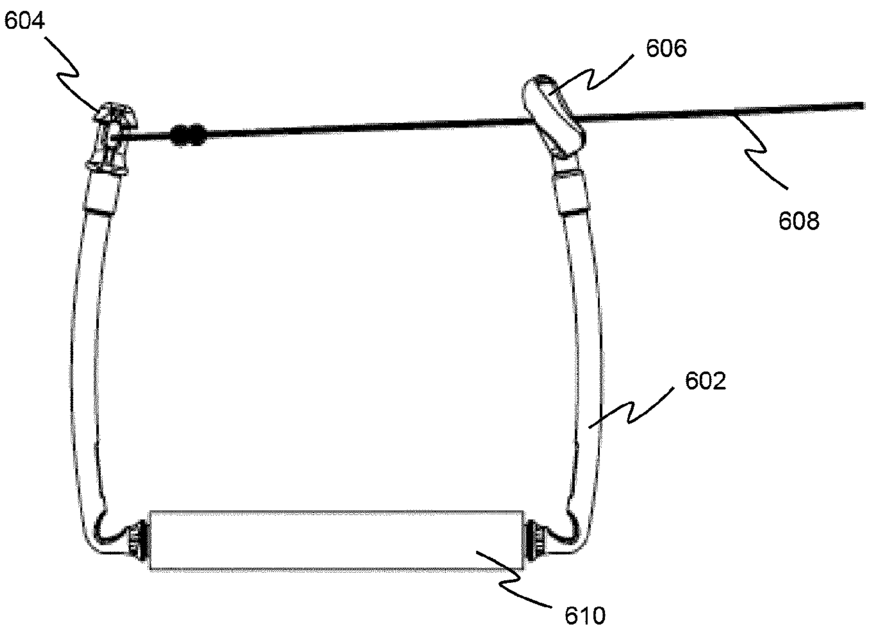
Figure 11C:
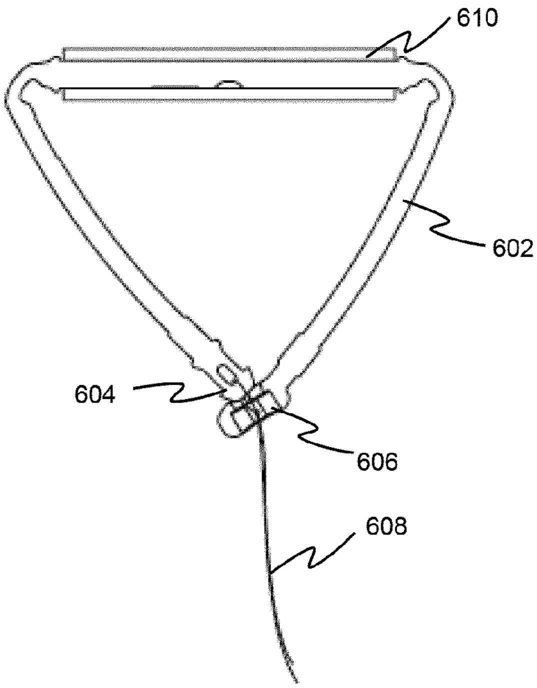
Figure 11D:
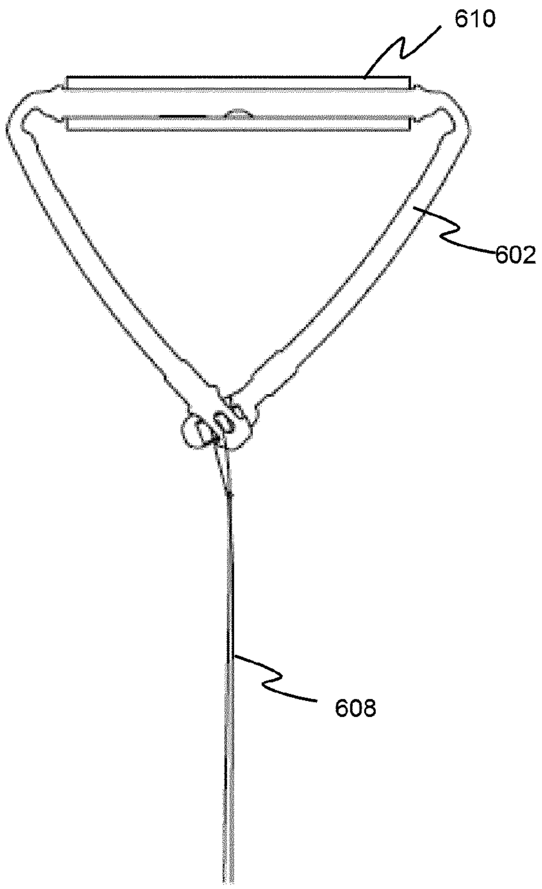

FIG. 11B shows the IUS in the form it can be stored in the sales package, i.e. before it is inserted inside the inserter, including a capsule 624 and a removal thread 626. FIGS. 11C and 11D illustrate the steps of closing and locking into shape of the IUS, once it is released inside the uterus. FIG. 11B shows how the frame 602 is bent by pulling on the removal thread 624. In FIG. 11C, the first end 604 of the frame 602 is in contact with the second end 606 of the frame, and in FIG. 11D, the first end 604 has been pulled through the second end 606, thus locking the IUS 600 into shape.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. An inserter for an intrauterine system, comprising:

a handle body having a distal end, a proximal end and a length $L_h$ defined as a distance between the distal end and the proximal end;

a measurement tube having a distal end and a proximal end, its proximal end being movably attached to the distal end of the handle body, provided the measurement tube is arranged to remain outside a cervix channel during insertion;

a plunger having a distal end, a proximal end, a length $L_p$ defined as a distance between the distal end and the proximal end, the plunger being movably arranged inside the handle body and the measurement tube, wherein the length $L_p$ is greater than the length $L_h$;

a flange movably arranged to surround the measurement tube;

a finger holder movably arranged to surround the handle body; and means for reversibly locking a removal thread of the intrauterine system, arranged on the handle body.

2. The inserter of claim 1, further comprising a piston attached to the plunger and arranged to move the plunger, the piston being movably arranged inside the handle body.

3. The inserter of claim 2, wherein the piston is hollow so as to allow the removal thread of the intrauterine system to pass through the piston.

4. The inserter of claim 2, wherein the piston comprises means for preventing its removal from inside the handle body.

5. The inserter of claim 1, wherein the means for reversibly locking the removal thread comprises a rotatable knob arranged, in a first position, to lock the removal thread between the handle body and the knob, and in a second position, to allow the removal thread to be moved with respect to the handle body.

6. The inserter of claim 5, wherein the knob and the handle body comprise corresponding forms allowing the removal threads to be locked when the knob is in the first position.

7. The inserter of claim 1, wherein the plunger is hollow so as to allow the removal thread of the intrauterine system to pass through the plunger.

8. The inserter of claim 1, wherein the plunger comprises means for preventing its removal from inside the handle body.

9. The inserter of claim 1, further comprising a tip cover having a distal end and a proximal end, the tip cover being arranged to withdraw inside the distal end of the measurement tube, provided the tip cover is arranged to remain outside the cervix channel during insertion.

10. The inserter of claim 1, wherein the length $L_h$ is 70-110 mm.

11. The inserter of claim 1, wherein the length $L_p$ is 50-90 mm.

12. The inserter of claim 1, wherein the proximal end of the measurement tube comprises insertion depth indicators.

13. A kit comprising an inserter according to claim 1 and an intrauterine system, wherein the intrauterine system comprises;

a frame having a first end, a second end and a length L defined as a distance from the first end to the second end;

a removal thread attached to the first end of the frame; and at least one pharmaceutically active agent;

wherein the first end of the frame comprises a first locking part and the second end of the frame comprises a second locking part, the first locking part and the second locking part being arranged to form a lock, the removal thread being configured to guide the first locking part to the second locking part.

14. The kit of claim 13, wherein the distal end of the plunger is configured to cooperate with the second locking part.

* * * * *